US009758796B2

(12) United States Patent
Fonfara et al.

(10) Patent No.: US 9,758,796 B2
(45) Date of Patent: Sep. 12, 2017

(54) NUCLEASE FUSION PROTEIN AND USES THEREOF

(75) Inventors: Ines Fonfara, Umeå (SE); Wolfgang Wende, Giessen (DE); Alfred Pingoud, Wetzlar (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 293 days.

(21) Appl. No.: 14/124,968

(22) PCT Filed: Jun. 8, 2012

(86) PCT No.: PCT/IB2012/052898
§ 371 (c)(1),
(2), (4) Date: Mar. 17, 2014

(87) PCT Pub. No.: WO2012/168910
PCT Pub. Date: Dec. 13, 2012

(65) Prior Publication Data
US 2014/0208457 A1    Jul. 24, 2014

Related U.S. Application Data

(60) Provisional application No. 61/495,410, filed on Jun. 10, 2011.

(30) Foreign Application Priority Data

Jun. 10, 2011   (EP) .................................... 11169567

(51) Int. Cl.
*C12N 1/20* (2006.01)
*C12N 15/90* (2006.01)
*C12N 9/22* (2006.01)

(52) U.S. Cl.
CPC ............. *C12N 15/902* (2013.01); *C12N 9/22* (2013.01); *C07K 2319/00* (2013.01); *C07K 2319/80* (2013.01)

(58) Field of Classification Search
CPC ........................ C07K 2319/80; C12N 15/902
USPC ....................................................... 435/199
See application file for complete search history.

(56) References Cited

U.S. PATENT DOCUMENTS

| | | | |
|---|---|---|---|
| 4,962,028 | A | 10/1990 | Bedbrook et al. |
| 5,352,605 | A | 10/1994 | Fraley et al. |
| 2011/0014338 | A1 | 1/2011 | Cloer |

FOREIGN PATENT DOCUMENTS

| | | |
|---|---|---|
| WO | WO 8402913 | 8/1984 |
| WO | WO 9519443 | 7/1995 |
| WO | WO 9945132 | 9/1999 |
| WO | WO 0027878 | 5/2000 |
| WO | WO 0046386 | 8/2000 |
| WO | WO 0153480 | 7/2001 |
| WO | WO 02057293 | 7/2002 |
| WO | WO 02057294 | 7/2002 |
| WO | WO 03062455 | 7/2003 |
| WO | WO 03078619 | 9/2003 |
| WO | WO 03080809 | 10/2003 |
| WO | WO 2004031346 | 4/2004 |
| WO | WO 2004037977 | 5/2004 |
| WO | WO 2006074956 | 7/2006 |
| WO | WO 2006134496 | 12/2006 |
| WO | WO 2007034262 | 3/2007 |
| WO | WO 2007047859 | 4/2007 |
| WO | WO 2007139898 | 12/2007 |
| WO | WO 2007148964 | 12/2007 |
| WO | WO 2008093249 | 8/2008 |
| WO | WO 2008102198 | 8/2008 |
| WO | WO 2008130629 | 10/2008 |
| WO | WO 2008152524 | 12/2008 |
| WO | WO 2009006297 | 1/2009 |
| WO | WO 2009076292 | 6/2009 |
| WO | WO 2009130695 | 10/2009 |
| WO | WO 2011064751 | 6/2011 |

OTHER PUBLICATIONS

Wright et al. (2005), The Plant Journal, 44: 693-705.*
Altschul et al., "Basic Local Alignment Search Tool," J. Mol. Biol., vol. 215, (1990), pp. 403-410.
Amann et al., "Tightly Regulated *tac*Promoter Vectors Useful for the Expression of Unfused and Fused Proteins in *Escherichia coli*," Gene, vol. 69, (1988), pp. 301-315.
Athanasiadis et al., "Complete Nucleotide Sequence of the *Pvu* II Restriction Enzyme Gene from *Proteus vulgaris*," Nucleic Acids Research, vol. 18, No. 21, (1990), p. 6434.
Baldari et al., "A Novel Leader Peptide Which Allows Efficient Secretion of a Fragment of Human Interleukin 1β in *Saccharomyces cerevisiae*," The EMBO Journal, vol. 6, No. 1, (1987), pp. 229-234.
Becker et al., "New Plant Binary Vectors with Selectable Markers Located Proximal to the Left T-DNA Border," Plant Molecular Biology, vol. 20, (1992), pp. 1195-1197.

(Continued)

*Primary Examiner* — Tekchand Saidha
(74) *Attorney, Agent, or Firm* — Marshall, Gerstein & Borun LLP

(57) ABSTRACT

The present invention is concerned with nuclease fusion proteins and various uses thereof. Specifically, it relates to a polynucleotide encoding a polypeptide comprising (i) a first module comprising at least a first DNA binding domain derived from a homing endonuclease, (ii) a linker, and (iii) a second module comprising at least a second DNA binding domain and a cleavage domain derived from a restriction endonuclease, wherein the polypeptide functionally interacts only with DNA comprising a DNA recognition site for the first DNA binding domain and a DNA recognition site for the second DNA binding domain, and wherein the cleavage domain cleaves DNA within a specific DNA cleavage site upon binding of the polypeptide. Further contemplated are a vector and a non-human transgenic organism comprising the polynucleotide as well as a polypeptide encoded by the polynucleotide of the invention. Finally, the present invention relates to a method for introducing a nucleic acid of interest into a genome of a non-human organism wherein the polypeptide of the invention is applied.

11 Claims, 6 Drawing Sheets

(56) References Cited

OTHER PUBLICATIONS

Benfey et al., "The CaMV 35S Enhancer Contains at Least Two Domains Which can Confer Different Developmental and Tissue-Specific Expression Patterns," The EMBO Journal, vol. 8, No. 8, (1989), pp. 2195-2202.

Bevan, "Binary *Agrobacterium* Vectors for Plant Transformation," Nucleic Acids Research, vol. 12, No. 22, (1984), pp. 8711-8721.

Christian et al., "Targeting DNA Double-Strand Breaks with TAL Effector Nucleases," Genetics, vol. 186, (2010), pp. 757-761.

D'Halluin et al., "Homologous Recombination: A Basis for Targeted Genome Optimization in Crop Species such as Maize," Plant Biotechnology Journal, vol. 6, (2008), pp. 93-102.

Doyon et al., "Directed Evolution and Substrate Specificity Profile of Homing Endonuclease I-Scel," J. Am. Chem. Soc., vol. 128, (2006), pp. 2477-2484.

Fonfara et al., "Creating Highly Specific Nucleases by Fusion of Active Restriction Endonucleases and Catalytically Inactive Homing Endonucleases," Nucleic Acids Research, (2011), pp. 1-14.

Gallie et al., "A Comparison of Eukaryotic Viral 5'-leader Sequences as Enhancers of mRNA Expression in vivo," Nucleic Acids Research, vol. 15, No. 21, (1987), pp. 8693-8711.

Gatz et al., "Stringent Repression and Homogeneous De-pression by Tetracycline of a Modified CaMV 35S Promoter in Intact Transgenic Tobacco Plants," The Plant Journal, vol. 2, No. 3, (1992), pp. 397-404.

Gatz, "Chemical Control of Gene Expression," Annu. Rev. Plant Physiol. Plant Mol. Biol., vol. 48, (1997), pp. 89-108.

Gielen et al., "The Complete Nucleotide Sequence of the TL-DNA of *Agrobacterium tumefaciens* Plasmid pTiAch5," The EMBO Journal, vol. 3, No. 4, (1984), pp. 835-846.

Gruen et al., "An in vivo Selection System for Homing Endonuclease Activity," Nucleic Acids Research, vol. 30, No. 7 e29, (2002), pp. 1-6.

Franck et al., "Nucleotide Sequence of Cauliflower Mosaic Virus DNA," Cell., vol. 21, (1980), pp. 285-294.

International Preliminary Report on Patentability, issued in PCT/IB2012/052898, dated Dec. 27, 2013.

International Search Report, issued in PCT/IB2012/052898, dated Oct. 18, 2012.

Kermode, "Mechanisms of Intracellular Protein Transport and Targeting in Plant Cells," Critical Reviews in Plant Sciences, vol. 15, No. 4, (1996), pp. 285-423.

Kirsch and Joly, "An Improved PCR-Mutagenesis Strategy for Two-Site Mutagenesis or Sequence Swapping Between Related Genes," Nucleic Acids Research, vol. 26, No. 7, (1998), pp. 1848-1850.

Kurjan and Herskowitz, "Structure of a Yeast Pheromone Gene (*MFα*): A Putative α-Factor Precursor Contains Four Tandem Copies of Mature α-Factor," Cell, vol. 30, (1992), pp. 933-943.

Lippow et al., "Creation of a Type IIS Restriction Endonuclease with a Long Recognition Sequence," Nucleic Acids Research, vol. 37, No. 9, (2009), pp. 3061-3073.

Luckow and Summers, "High Level Expression of Nonfused Foreign Genes with *Autographa californica* Nuclear Polyhedrosis Virus Expression Vectors," Virology, vol. 170, (1989), pp. 31-39.

Moure et al., "The Crystal Structure of the Gene Targeting Homing Endonuclease I-*Scel* Reveals the Origins of its Target Site Specificity," J. Mol. Biol., vol. 334, (2003), pp. 685-695.

Needleman and Wunsch, "A General Method Applicable to the Search for Similarities in the Amino Acid Sequence of Two Proteins," J. Mol. Biol., vol. 48, (1970), pp. 443-453.

Pingoud et al., "Type II Restriction Endonucleases: Structure and Mechanism," Cell. Mol. Life Sci., vol. 62, (2005), pp. 685-707.

Rice et al., "EMBOSS: The European Molecular Biology Open Software Suite," TIG, vol. 16, No. 6, (2000), pp. 276-277.

Schultz et al., "Expression and Secretion in Yeast of a 400-kDa Envelop Glycoprotein Derived from Epstein-Barr Virus," Gene, vol. 54, (1987), pp. 113-123.

Smith and Johnson, "Single-Step Purification of Polypeptides Expressed in *Escherichia coli* as Fusions with Glutathione S-Transferase," Gene, vol. 67, (1988), pp. 31-40.

Smith et al., "Production of Human Beta Interferon in Insect Cells Infected with a Baculovirus Expression Vector," Molecular and Cellular Biology, vol. 3, No. 12, (1983), pp. 2156-2165.

Steuer et al., "Chimeras of the Homing Endonuclease PI-Scel and the Homologous *Candida tropicalis* Intein: A Study to Explore the Possibility of Exchanging DNA-Binding Modules to Obtain Highly Specific Endonucleases with Altered Specificity," ChemBioChem, vol. 5, (2004), pp. 206-213.

Stoddard, "Homing Endonuclease Structure and Function," Quarterly Reviews of Biophysics, vol. 38, No. 1, (2006), pp. 49-95.

Studier et al., "Use of T7 RNA Polymerase to Direct Expression of Cloned Genes," Methods in Enzymology, vol. 185, pp. 60-89.

Van Den Hondel and Punt, "Gene Transfer Systems and Vector Development for Filamentous Fungi," Applied Molecular Genetics of Fungi, Symposium of the British Mycological Society, eds. Peberdy et al., Cambridge University Press, (1991), pp. 1-28.

Van Den Hondel et al., "Heterologous Gene Expression in Filamentous Fungi," More Gene Manipulations in Fungi, eds. Bennett and Lasure, Academic Press, Inc., (1991), pp. 396-428.

Wah et al., "Structure of *Fokl* has Implications for DNA Cleavage," Proc. Natl. Acad. Sci. USA, vol. 95, (1998), pp. 10564-10569.

Westmoreland et al., "Blunt-Ended DNA Double-Strand Breaks Induced by Endonucleases Pvull and EcoRV are Poor Substrates for Repair in *Saccharomyces cerevisiae*," DNA Repair (Amst.), vol. 9, No. 6, (2010), pp. 617-626.

White, "Vectors for Gene Transfer in Higher Plants," Transgenic Plants, vol. 1, eds. Kung and Wu, Academic Press, Inc., (1993), pp. 15-48.

Wright et al., "High-Frequency Homologous Recombination in Plants Mediated by Zinc-Finger Nucleases," The Plant Journal, vol. 44, (2005), pp. 693-705.

\* cited by examiner

A:

B:

A:

B:

C:

SEQUENCE LISTING

```
<160> NUMBER OF SEQ ID NOS: 13

<210> SEQ ID NO 1
<211> LENGTH: 235
<212> TYPE: PRT
<213> ORGANISM: Saccharomyces cerevisiae

<400> SEQUENCE: 1

Met Lys Asn Ile Lys Lys Asn Gln Val Met Asn Leu Gly Pro Asn Ser
1               5                  10                  15

Lys Leu Leu Lys Glu Tyr Lys Ser Gln Leu Ile Glu Leu Asn Ile Glu
```

```
                    20                  25                  30
Gln Phe Glu Ala Gly Ile Gly Leu Ile Leu Gly Asp Ala Tyr Ile Arg
                35                  40                  45

Ser Arg Asp Glu Gly Lys Thr Tyr Cys Met Gln Phe Glu Trp Lys Asn
 50                  55                  60

Lys Ala Tyr Met Asp His Val Cys Leu Leu Tyr Asp Gln Trp Val Leu
 65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
                100                 105                 110

Ala Asn Leu Phe Ile Val Asn Lys Lys Thr Ile Pro Asn Asn Leu
                115                 120                 125

Val Glu Asn Tyr Leu Thr Pro Met Ser Leu Ala Tyr Trp Phe Met Asp
                130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
                180                 185                 190

Lys Asn Lys Pro Ile Ile Tyr Ile Asp Ser Met Ser Tyr Leu Ile Phe
                195                 200                 205

Tyr Asn Leu Ile Lys Pro Tyr Leu Ile Pro Gln Met Met Tyr Lys Leu
                210                 215                 220

Pro Asn Thr Ile Ser Ser Glu Thr Phe Leu Lys
225                 230                 235

<210> SEQ ID NO 2
<211> LENGTH: 159
<212> TYPE: PRT
<213> ORGANISM: Proteus vulgaris

<400> SEQUENCE: 2

Met Ser His Pro Asp Leu Asn Lys Leu Leu Glu Leu Trp Pro His Ile
 1               5                  10                  15

Gln Glu Tyr Gln Asp Leu Ala Leu Lys His Gly Ile Asn Asp Ile Phe
                20                  25                  30

Gln Asp Asn Gly Gly Lys Leu Leu Gln Val Leu Leu Ile Thr Gly Leu
                35                  40                  45

Thr Val Leu Pro Gly Arg Glu Gly Asn Asp Ala Val Asp Asn Ala Gly
 50                  55                  60

Gln Glu Tyr Glu Leu Lys Ser Ile Asn Ile Asp Leu Thr Lys Gly Phe
 65                  70                  75                  80

Ser Thr His His His Met Asn Pro Val Ile Ile Ala Lys Tyr Arg Gln
                85                  90                  95

Val Pro Trp Ile Phe Ala Ile Tyr Arg Gly Ile Ala Ile Glu Ala Ile
                100                 105                 110

Tyr Arg Leu Glu Pro Lys Asp Leu Glu Phe Tyr Tyr Asp Lys Trp Glu
                115                 120                 125

Arg Lys Trp Tyr Ser Asp Gly His Lys Asp Ile Asn Asn Pro Lys Ile
                130                 135                 140

Pro Val Lys Tyr Val Met Glu His Gly Thr Lys Ile Tyr Gly Ser
145                 150                 155
```

<210> SEQ ID NO 3
<211> LENGTH: 6
<212> TYPE: PRT
<213> ORGANISM: artificial
<220> FEATURE:
<223> OTHER INFORMATION: linker sequence

<400> SEQUENCE: 3

Ala Ser Arg Thr Thr Gly
1               5

<210> SEQ ID NO 4
<211> LENGTH: 10
<212> TYPE: PRT
<213> ORGANISM: artificial
<220> FEATURE:
<223> OTHER INFORMATION: linker sequence

<400> SEQUENCE: 4

Ala Ser Thr Lys Gln Leu Val Lys Ser Gly
1               5                   10

<210> SEQ ID NO 5
<211> LENGTH: 10
<212> TYPE: PRT
<213> ORGANISM: artificial
<220> FEATURE:
<223> OTHER INFORMATION: linker sequence

<400> SEQUENCE: 5

Ala Ser Gly Gly Ser Gly Ser Gly Ser Gly
1               5                   10

<210> SEQ ID NO 6
<211> LENGTH: 10
<212> TYPE: PRT
<213> ORGANISM: artificial
<220> FEATURE:
<223> OTHER INFORMATION: linker sequence

<400> SEQUENCE: 6

Ala Ser Gly Asp Ser Gly Ser Asp Ser Gly
1               5                   10

<210> SEQ ID NO 7
<211> LENGTH: 1167
<212> TYPE: DNA
<213> ORGANISM: artificial
<220> FEATURE:
<223> OTHER INFORMATION: nucleic acid sequence PSs (NA) L0TY

<400> SEQUENCE: 7
atgggtcacc cagatctaaa taaattatta gagctttggc cgcatataca ggaatatcaa      60
gacttagcat aaaacatgg aataaatgat attttcaag ataatggtgg aaagttgctt      120
caagtccttc taattacagg attaacagta ctaccaggac gagaaggtaa tgatgctgta      180
gataacgcag acaagaata cgagttaaaa tcaataaaca tagacctcac taaaggtttt      240
tcaactcacc accacatgaa tcctgtaatt attgcaaaat atagacaagt accttggatt      300
tttgccatat accgtggtat cgcaatagaa gctatataca gattagagcc aaaagatcta      360
gaattttact atgataaatg ggaaggaaa tggtattcag atgggcataa agatattaac      420
aaccctaaaa tacctgtaaa atatgtaatg gaacatggga caaagattta cgctagccgt      480
acgaccggta tgcataacat caaaaaaaac caggtaatga acctgggtcc gaactctaaa      540

-continued

```
ctgctgaaag aatacaaatc ccagctgatc gaactgaaca tcgaacagtt cgaagcaggt      600
atcggtctga tcctgggaaa cgcttacatc cgttcacgtg atgaaggtaa aacctactgt      660
atgcagttcg agtggaaaaa caaagcatac atggaccacg tatgtctgct gtacgatcag      720
tgggtactgt ccccgccgca caaaaaagaa cgtgttaacc acctgggtaa cctggtaatc      780
acctggggcg cccagacttt caaacaccaa gctttcaaca aactggctaa cctgttcatc      840
gttaacaaca aaaaaaccat cccgaacaac ctggttgaaa actacctgac cccgatgtct      900
ctggcatact ggttcatgga tgccggcggt aaatgggatt acaacaaaaa ctctaccaac      960
aaatcgatcg tactgaacac ccagtctttc actttcgaag aagtagaata cctggttaag     1020
ggtctgcgta acaaattcca actgaactgt acgtaaaaa tcaacaaaaa caaaccgatc      1080
atctacatcg attctatgtc ttacctgatc ttctacaacc tgatcaaacc gtacctgatc     1140
ccacagatga tgtacaaact gccgaac                                          1167
```

<210> SEQ ID NO 8
<211> LENGTH: 1179
<212> TYPE: DNA
<213> ORGANISM: artificial
<220> FEATURE:
<223> OTHER INFORMATION: nucleic acid sequence PSs (NA) FokTY

<400> SEQUENCE: 8

```
atgggtcacc cagatctaaa taaattatta gagctttggc cgcatataca ggaatatcaa       60
gacttagcat taaacatgg aataaatgat attttttcaag ataatggtgg aaagttgctt      120
caagtccttc taattacagg attaacagta ctaccaggac gagaaggtaa tgatgctgta      180
gataacgcag acaagaata cgagttaaaa tcaataaaca tagacctcac taaaggtttt      240
tcaactcacc accacatgaa tcctgtaatt attgcaaaat atagacaagt accttggatt      300
tttgccatat accgtggtat cgcaatagaa gctatataca gattagagcc aaaagatcta      360
gaattttact atgataaatg ggaaaggaaa tggtattcag atgggcataa agatattaac      420 aacccctaaaa tacctgtaaa atatgtaatg gaacatggga caaagattta cgctagcacc      480
aaacagctgg ttaagtccgg tatgcataac atcaaaaaaa accaggtaat gaacctgggt      540
ccgaactcta aactgctgaa agaatacaaa tcccagctga tcgaactgaa catcgaacag      600
ttcgaagcag gtatcggtct gatcctggga acgcttaca tccgttcacg tgatgaaggt      660
aaaacctact gtatgcagtt cgagtggaaa aacaaagcat acatggacca cgtatgtctg      720
ctgtacgatc agtgggtact gtccccgccg cacaaaaaag aacgtgttaa ccacctgggt      780
aacctggtaa tcacctgggg cgcccagact ttcaaacacc aagctttcaa caaactggct      840
aacctgttca tcgttaacaa caaaaaaacc atcccgaaca acctggttga aaactacctg      900
accccgatgt ctctggcata ctggttcatg gatgccggcg gtaaatggga ttacaacaaa      960
aactctacca caaatcgat cgtactgaac acccagtctt tcactttcga agaagtagaa     1020
tacctggtta agggtctgcg taacaaattc caactgaact gttacgtaaa aatcaacaaa     1080
aacaaaccga tcatctacat cgattctatg tcttacctga tcttctacaa cctgatcaaa     1140
ccgtacctga tcccacagat gatgtacaaa ctgccgaac                            1179
```

<210> SEQ ID NO 9
<211> LENGTH: 389
<212> TYPE: PRT
<213> ORGANISM: artificial
<220> FEATURE:

<223> OTHER INFORMATION: protein PSs (NA) F0TY

<400> SEQUENCE: 9

```
Met Gly His Pro Asp Leu Asn Lys Leu Leu Glu Leu Trp Pro His Ile
1               5                   10                  15

Gln Glu Tyr Gln Asp Leu Ala Leu Lys His Gly Ile Asn Asp Ile Phe
            20                  25                  30

Gln Asp Asn Gly Gly Lys Leu Leu Gln Val Leu Leu Ile Thr Gly Leu
        35                  40                  45

Thr Val Leu Pro Gly Arg Glu Gly Asn Asp Ala Val Asp Asn Ala Gly
    50                  55                  60

Gln Glu Tyr Glu Leu Lys Ser Ile Asn Ile Asp Leu Thr Lys Gly Phe
65                  70                  75                  80

Ser Thr His His His Met Asn Pro Val Ile Ile Ala Lys Tyr Arg Gln
                85                  90                  95

Val Pro Trp Ile Phe Ala Ile Tyr Arg Gly Ile Ala Ile Glu Ala Ile
            100                 105                 110

Tyr Arg Leu Glu Pro Lys Asp Leu Glu Phe Tyr Tyr Asp Lys Trp Glu
            115                 120                 125

Arg Lys Trp Tyr Ser Asp Gly His Lys Asp Ile Asn Asn Pro Lys Ile
130                 135                 140

Pro Val Lys Tyr Val Met Glu His Gly Thr Lys Ile Tyr Ala Ser Arg
145                 150                 155                 160

Thr Thr Gly Met His Asn Ile Lys Lys Asn Gln Val Met Asn Leu Gly
                165                 170                 175

Pro Asn Ser Lys Leu Leu Lys Glu Tyr Lys Ser Gln Leu Ile Glu Leu
            180                 185                 190

Asn Ile Glu Gln Phe Glu Ala Gly Ile Gly Leu Ile Leu Gly Asn Ala
        195                 200                 205

Tyr Ile Arg Ser Arg Asp Glu Gly Lys Thr Tyr Cys Met Gln Phe Glu
    210                 215                 220

Trp Lys Asn Lys Ala Tyr Met Asp His Val Cys Leu Leu Tyr Asp Gln
225                 230                 235                 240

Trp Val Leu Ser Pro Pro His Lys Lys Glu Arg Val Asn His Leu Gly
                245                 250                 255

Asn Leu Val Ile Thr Trp Gly Ala Gln Thr Phe Lys His Gln Ala Phe
            260                 265                 270

Asn Lys Leu Ala Asn Leu Phe Ile Val Asn Asn Lys Thr Ile Pro
        275                 280                 285

Asn Asn Leu Val Glu Asn Tyr Leu Thr Pro Met Ser Leu Ala Tyr Trp
    290                 295                 300

Phe Met Asp Ala Gly Gly Lys Trp Asp Tyr Asn Lys Asn Ser Thr Asn
305                 310                 315                 320

Lys Ser Ile Val Leu Asn Thr Gln Ser Phe Thr Phe Glu Glu Val Glu
                325                 330                 335

Tyr Leu Val Lys Gly Leu Arg Asn Lys Phe Gln Leu Asn Cys Tyr Val
            340                 345                 350

Lys Ile Asn Lys Asn Lys Pro Ile Ile Tyr Ile Asp Ser Met Ser Tyr
        355                 360                 365

Leu Ile Phe Tyr Asn Leu Ile Lys Pro Tyr Leu Ile Pro Gln Met Met
    370                 375                 380

Tyr Lys Leu Pro Asn
385
```

<210> SEQ ID NO 10
<211> LENGTH: 393
<212> TYPE: PRT
<213> ORGANISM: artificial
<220> FEATURE:
<223> OTHER INFORMATION: Prt PSs (NA) FokTY

<400> SEQUENCE: 10

```
Met Gly His Pro Asp Leu Asn Lys Leu Leu Glu Leu Trp Pro His Ile
1               5                   10                  15

Gln Glu Tyr Gln Asp Leu Ala Leu Lys His Gly Ile Asn Asp Ile Phe
            20                  25                  30

Gln Asp Asn Gly Gly Lys Leu Leu Gln Val Leu Leu Ile Thr Gly Leu
        35                  40                  45

Thr Val Leu Pro Gly Arg Glu Gly Asn Asp Ala Val Asp Asn Ala Gly
    50                  55                  60

Gln Glu Tyr Glu Leu Lys Ser Ile Asn Ile Asp Leu Thr Lys Gly Phe
65                  70                  75                  80

Ser Thr His His His Met Asn Pro Val Ile Ile Ala Lys Tyr Arg Gln
                85                  90                  95

Val Pro Trp Ile Phe Ala Ile Tyr Arg Gly Ile Ala Ile Glu Ala Ile
            100                 105                 110

Tyr Arg Leu Glu Pro Lys Asp Leu Glu Phe Tyr Tyr Asp Lys Trp Glu
        115                 120                 125

Arg Lys Trp Tyr Ser Asp Gly His Lys Asp Ile Asn Asn Pro Lys Ile
    130                 135                 140

Pro Val Lys Tyr Val Met Glu His Gly Thr Lys Ile Tyr Ala Ser Thr
145                 150                 155                 160

Lys Gln Leu Val Lys Ser Gly Met His Asn Ile Lys Lys Asn Gln Val
                165                 170                 175

Met Asn Leu Gly Pro Asn Ser Lys Leu Leu Lys Glu Tyr Lys Ser Gln
            180                 185                 190

Leu Ile Glu Leu Asn Ile Glu Gln Phe Glu Ala Gly Ile Gly Leu Ile
        195                 200                 205

Leu Gly Asn Ala Tyr Ile Arg Ser Arg Asp Glu Gly Lys Thr Tyr Cys
    210                 215                 220

Met Gln Phe Glu Trp Lys Asn Lys Ala Tyr Met Asp His Val Cys Leu
225                 230                 235                 240

Leu Tyr Asp Gln Trp Val Leu Ser Pro Pro His Lys Lys Glu Arg Val
                245                 250                 255

Asn His Leu Gly Asn Leu Val Ile Thr Trp Gly Ala Gln Thr Phe Lys
            260                 265                 270

His Gln Ala Phe Asn Lys Leu Ala Asn Leu Phe Ile Val Asn Asn Lys
        275                 280                 285

Lys Thr Ile Pro Asn Asn Leu Val Glu Asn Tyr Leu Thr Pro Met Ser
    290                 295                 300

Leu Ala Tyr Trp Phe Met Asp Ala Gly Gly Lys Trp Asp Tyr Asn Lys
305                 310                 315                 320

Asn Ser Thr Asn Lys Ser Ile Val Leu Asn Thr Gln Ser Phe Thr Phe
                325                 330                 335

Glu Glu Val Glu Tyr Leu Val Lys Gly Leu Arg Asn Lys Phe Gln Leu
            340                 345                 350

Asn Cys Tyr Val Lys Ile Asn Lys Asn Lys Pro Ile Ile Tyr Ile Asp
        355                 360                 365
```

```
Ser Met Ser Tyr Leu Ile Phe Tyr Asn Leu Ile Lys Pro Tyr Leu Ile
    370                 375                 380

Pro Gln Met Met Tyr Lys Leu Pro Asn
385                 390

<210> SEQ ID NO 11
<211> LENGTH: 54
<212> TYPE: DNA
<213> ORGANISM: Artificial Sequence
<220> FEATURE:
<223> OTHER INFORMATION: tripartite DNA recognition site

<400> SEQUENCE: 11
tagggataac agggtaatgg tactcagctg attcatatta ccctgttatc ccta        54

<210> SEQ ID NO 12
<211> LENGTH: 54
<212> TYPE: DNA
<213> ORGANISM: artificial sequence
<220> FEATURE:
<223> OTHER INFORMATION: tripartite DNA recognition site

<400> SEQUENCE: 12
tagggataac agggtaatat gaatcagctg agtaccatta ccctgttatc ccta        54

<210> SEQ ID NO 13
<211> LENGTH: 54
<212> TYPE: DNA
<213> ORGANISM: artificial
<220> FEATURE:
<223> OTHER INFORMATION: tripartite DNA recognition site
<220> FEATURE:
<221> NAME/KEY: misc_feature
<222> LOCATION: (19)..(24)
<223> OTHER INFORMATION: n is a, c, g, or t
<220> FEATURE:
<221> NAME/KEY: misc_feature
<222> LOCATION: (31)..(36)
<223> OTHER INFORMATION: n is a, c, g, or t

<400> SEQUENCE: 13
tagggataac agggtaatnn nnnncagctg nnnnnnatta ccctgttatc ccta        54
```

NUCLEASE FUSION PROTEIN AND USES THEREOF

This application is a National Stage application of International Application No. PCT/IB2012/052898, filed Jun. 8, 2012, which claims the benefit of U.S. Provisional Application No. 61/495,410, filed Jun. 10, 2011. This application also claims priority under 35 U.S.C. §119 to European Patent Application No. 11169567.2, filed Jun. 10, 2011.

The present invention is concerned with nuclease fusion proteins and various uses thereof. Specifically, it relates to a polynucleotide encoding a polypeptide comprising (i) a first module comprising at least a first DNA binding domain derived from a homing endonuclease, (ii) a linker, and (iii) a second module comprising at least a second DNA binding domain and a cleavage domain derived from a restriction endonuclease, wherein said polypeptide functionally interacts only with DNA comprising a DNA recognition site for the first DNA binding domain and a DNA recognition site for the second DNA binding domain, and wherein said cleavage domain cleaves DNA within a specific DNA cleavage site upon binding of the polypeptide. Further contemplated by the invention are a vector, a non-human transgenic organism comprising said polynucleotide as well as a polypeptide encoded by the polynucleotide of the invention. Finally, the present invention relates to a method for introducing a nucleic acid of interest into a genome of a non-human organism wherein the polypeptide of the invention is applied.

Restriction endonucleases are important tools for molecular cloning of DNA. These enzymes are required for the cleavage of DNA at specific recognition and cleavage sites, thereby allowing the reproducible generation of defined DNA fragments. Moreover, said defined fragments generated by the restriction endonucleases can be combined with other DNA molecules and, in particular, with vectors in ligation reactions for the purpose of molecular cloning. The principles of how restriction endonucleases can be used for molecular cloning are well known for many years.

Many restriction endonucleases have been characterized in the past from many different prokaryotic organisms. There is a need for restriction endonucleases which rarely cleave genomic DNA, i.e. those whose DNA recognition and cleavage sites occur only at a limited number in the genome. There are rarely cleaving, naturally occurring endonucleases known in the art. However, most of said restriction endonucleases cleave statistically more than once in a genome. Artificial enzymes have been more recently generated which statistically cleave less often and sometimes even once in a genome.

Artificial fusion proteins comprising zinc-finger domains for DNA binding and the non-specific DNA cleavage domain of the restriction endonuclease FokI have been reported in the prior art (Wah 1998, Proc. Natl. Acad. Sci. USA 95: 10564-10569; WO2003/080809; WO2007/139898; WO2002/057294; WO2000/27878; WO1999/45132; WO2003/062455; WO2002/057293). Instead of zinc-finger domains, transcription activator-like effectors (TALEs) were reported as a suitable basis for nucleases of very high specificity when fused to the non-specific DNA cleavage domain of FokI (Christian 2010, Genetics 186(2): 757-U476).

Other approaches for generating artificial, rarely-cleaving meganucleases are based on homing endonucleases such as LAGLIDADG homing endonucleases and, in particular, of I-CreI or I-SceI (WO2009/076292; WO2007/047859; WO2008/152524; WO2008/102198; WO2008/093249; WO2007/034262; WO2003/078619; Doyon 2006, J Am Chem Soc 128: 2477-2484). Artificial fusion proteins comprising a homing endonuclease such as I-SceI and the non-specific DNA cleavage domain of FokI have also been reported (Lippow 2009, Nucleic Acid Res 37(9): 3061-3073).

Moreover, the rare cutting endonucleases have been reported to facilitate homologous recombination and other integration of DNA fragments into a genome in vivo (WO2003/080809; WO2000/46386; WO2009/006297; WO2006/074956; WO2006/134496; WO2007/148964; WO2009/130695). Accordingly, these enzymes can be used for the generation of various types of transgenic organisms.

Thus, there is a need for further rare cutting endonucleases and, in particular, for those which cleave at a defined DNA cleavage site and which produce suitable cleavage products which can be recognized and used by the endogenous DNA repair system of an organism such that integration of a DNA of interest into the genome of the said organism will be facilitated.

Thus, the technical problem underlying the present invention could be seen as the provision of means and methods for complying with the aforementioned needs. The technical problem is solved by the embodiments characterized in the claims and herein below.

Therefore, the present invention relates to a polynucleotide encoding a polypeptide comprising:
(i) a first module comprising at least a first DNA binding domain derived from a homing endonuclease;
(ii) a linker; and
(iii) a second module comprising at least a second DNA binding domain and a cleavage domain derived from a restriction endonuclease;
wherein said polypeptide functionally interacts only with DNA comprising a DNA recognition site for the first DNA binding domain and a DNA recognition site for the second DNA binding domain, and
wherein said cleavage domain cleaves DNA within a specific DNA cleavage site upon binding of the polypeptide.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecules. The polynucleotide may be, preferably, a linear or circular molecule. Moreover, in addition to the nucleic acid sequences encoding the aforementioned polypeptide, a polynucleotide of the present invention may comprise additional sequences required for proper transcription and/or translation such as 5'- or 3'-UTR sequences.

The term "first module" as used herein refers to a first structural and/or functional part of the polypeptide encoded by the polynucleotide of the invention. Said first module, preferably, comprises or essentially consists of at least a first DNA binding domain. DNA binding as used herein refers to the capability of a polypeptide or domain thereof to physically bind to DNA. Such a polypeptide or domain thereof is or comprises a DNA binding domain. DNA binding occurs at a defined nucleotide sequence within a DNA molecule referred to herein also as DNA recognition site of the DNA binding domain. The first module may also comprise, in addition to the first DNA binding domain, further domains. Such further domains, preferably, can be DNA binding domains as well or other domains which mediate interaction with regulatory proteins or transport proteins, e.g., interaction domains for nuclear transport regulating proteins. It will be understood that, preferably, the said first DNA binding domain can also be comprised in the first module as a complete DNA binding protein, such as a naturally occurring homing endonuclease, a genetically modified homing endonuclease or an artificial fusion protein of such a homing endonuclease with another DNA binding protein, e.g., a zinc-finger DNA binding protein or a DNA binding transcription factor. Details of preferred DNA binding domains which can be applied in accordance with the present invention are described elsewhere herein.

Preferably, said first module exhibits reduced or no catalytic activity with respect to DNA cleavage. Preferably, a reduced catalytic activity as referred to in accordance with the present invention can be determined by measuring DNA cleavage elicited by the first module of the polypeptide encoded by the polynucleotide of the present invention and a corresponding wild type homing endonuclease comprising the first DNA binding domain, i.e. a comparison with respect to the DNA cleavage activity of the homing endonuclease from which the at least first DNA binding domain in the first module has been derived. Reduced as used in the context of the present invention means reduced to a statistically significant extent and, preferably, to a reduction of at least 70%, at least 80%, at least 90%, at least 99%, at least 99.9%, at least 99.99%, at least 99.999%, or at least 99.9999%. Whether a reduction is statistically significant can be determined by the skilled artisan without further ado by standard techniques of statistics.

The term "homing endonuclease" as used herein refers to endonucleases which are typically encoded by introns or inteins. Naturally occurring homing endonucleases, similar to transposons, allow for the perpetuation of the genetic elements that encode them in that they, usually, cleave the DNA of the intron- or intein-less allele of the recipient organism. The DNA recognition sites of homing endonucleases are long enough to occur randomly only with a very low probability, preferably approximately once every $10^7$ bp up to once every $10^9$ bp or even with a lower probability. Preferably, the DNA recognition sites recognized by the DNA binding domains of homing endonucleases, in contrast to those of other endonucleases, consist of at least 10, at least 12, at least 14, at least 16, at least 18, at least 20, at least 30 or at least 40 contiguous nucleotides. Preferably, said recognition sites are asymmetric. Upon cleavage of the DNA of the intro- or intein-less allele, the cellular DNA repair system is activated, whereby the intron- or intein containing gene is supplied in trans, the so called "homing" process.

There are five different families of homing endonucleases. The members of the LAGLIDADG family of homing endonucleases each have one or two LAGLIDADG motifs per polypeptide chain. The LAGLIDADG amino acid sequence is a conserved sequence directly involved in domain-domain and subunit-subunit interaction and the DNA cleavage process. Those enzymes that have only one motif per polypeptide chain act as homodimers, while those having two motifs act as monomers. The members of the GIY-YIG family of homing endonucleases have one GIY-YIG motif as the catalytic motif that is associated with a DNA binding motif. The prototypic enzyme of this family is I-TevI. The members of the His-Cys box family of homing endonucleases contain a stretch of 30 amino acids including two conserved histidines and three conserved cysteines. I-PpoI is a member of said family and acts as a monomer. The members of the H-N-H family of homing endonucleases are characterized by a consensus sequence of approximately 30 amino acids having two pairs of conserved histidines and one asparagine. The said conserved amino acids form an alpha-beta-beta-alpha (αββα) metal finger motif. The PD . . . D/EXK family of homing endonucleases are characterized by a structural core that consists of a four-stranded beta sheet flanked by alpha helices that harbors the characteristic PD . . . D/EXK active site motif (see, e.g., Pingoud 2005, Cell Mol Life Sci 62(6): 685-707).

As referred to above, a first DNA binding domain according to the invention is a DNA binding domain of a homing endonuclease. Preferred homing endonucleases from which such a first DNA binding domain can be derived are selected from the group consisting of: LAGLIDADG-family homing endonucleases, GIY-YIG family homing nucleases, His-Cys-box family homing endonucleases, H-N-H family homing endonucleases and PD . . . D/EXK family homing endonucleases. Preferred members of said homing endonuclease families which can be used for deriving DNA binding domains to be included into the polypeptide encoded by the polynucleotide of the present invention are F-CphI, F-EcoT5I, F-EcoT5II, F-EcoT5IV, F-PhiU5I, F-SceI, F-SceII, F-TevI, F-TevII, F-TevIII, F-TevIV, H-DreI, I-AniI, I-ApeKI, I-BanI, I-BasI, I-BmoI, I-BthII, I-BthORFAP, I-CeuI, I-ChuI, I-CmoeI, I-CpaI, I-CpaII, I-CreI, I-CreII, I-CsmI, I-CvuI, I-DdiI, I-DmoI, I-HmuI, I-HmuII, I-LlaI, I-LtrI, I-LtrWI, I-MsoI, I-NanI, I-NitI, I-NjaI, I-OnuI, I-PakI, I-PogI, I-PorI, I-PpoI, I-ScaI, I-SceI, I-SceII, I-SceIII, I-SceIV, I-SceV, I-SceVI, I-SceVII, I-SpomI, I-Ssp6803I, I-TevI, I-TevII, I-TevIII, I-Tsp061I, I-TwoI, I-Vdi141I, PI-MgaI, PI-MIeSI, PI-MtuI, PI-PabI, PI-PabII, PI-PfuI, PI-PfuII, PI-PkoI, PI-PkoII, PI-PspI, PI-ScaI, PI-SceI, PI-TfuI, PI-TfuII, PI-ThyI, PI-TliI, PI-TliII, PI-TmaI, PI-TmaKI, and PI-ZbaI.

More preferably, said first DNA binding domain comprised in the first module is derived from a homing endonuclease of the LAGLIDADG-family. Even more preferably, said first DNA binding domain comprised in the first module is derived from I-SceI. Most preferably, said DNA binding domain is derived from I-SceI or a variant thereof and comprises at least one of following modifications: substitution D44S alone or in combination with D145A, or substitution D44N in combination with D145A. The positions of the modifications referred to before are indicated for the wild type I-SceI protein. These modifications inactivate the catalytic domain of I-SceI which is required for DNA cleavage so that the modified I-SceI either lacks the capability to cleave DNA or at least has reduced DNA cleavage activity while the DNA binding properties are essentially maintained. It is to be understood that the aforementioned amino acid positions will vary if modified variants of the I-SceI protein are used. Nevertheless, it is envisaged that DNA binding domains from such variants, preferably, also comprise at least one of the modifications at a corresponding position in their amino acid sequences which, preferably, also results in a loss or reduction of the DNA cleavage activity. The DNA cleavage activity of a modified variant can be determined by the skilled artisan without further ado, e.g., by using the assays described in the accompanying Examples, below. The amino acid sequence of I-SceI is well known in the art and described, e.g., in Pingoud 2005, loc cit. Moreover, nucleic acid sequences encoding said I-SceI amino acid sequences have also been described and can be derived from the amino acid sequence by the skilled artisan without further ado taking into account the degeneracy of the genetic code.

In a particular preferred embodiment, said I-SceI wild type sequence has an amino acid sequence as shown in SEQ ID NO: 1 or is a variant thereof having an amino acid sequence which differs from SEQ ID NO: 1 by at least one amino acid substitution, deletion and/or addition.

Preferably, such a variant of I-SceI has an amino acid sequence which is at least 70%, at least 80%, at least 90%, at least 95%, at least 98% or at least 99% identical with SEQ ID NO: 1 and, preferably, comprises a DNA binding domain having essentially the same DNA binding activity as the DNA binding domain of I-SceI shown in SEQ ID NO: 1. Sequence identity as used herein is, preferably, to be determined by way of alignment over the entire length of an amino acid or nucleic acid sequence or over a contiguous stretch of amino acids or nucleotides, respectively. Said stretch being at least 50% in length of the reference sequence to which a given sequences shall be compared. A preferred algorithm for determining the percentage of sequence identity is the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice 2000, Trends in Genetics 16(6), 276-277), using either a BLOSUM 45 or PAM250 scoring matrix for distantly related proteins, or either a BLOSUM 62 or PAM160 scoring matrix for more closely related proteins, and a gap opening penalty of 16, 14, 12, 10, 8, 6, or 4 and a gap extension penalty of 0.5, 1, 2, 3, 4, 5, or 6. Guides for local installation of the EMBOSS package as well as links to WEB-Services can be found at http://emboss.sourceforge.net. Preferred parameters to be used for aligning two amino acid sequences using the needle program are the default parameters, including the EBLOSUM62 scoring matrix, a gap opening penalty of 10 and a gap extension penalty of 0.5. Also preferably, the percent identity between two nucleotide sequences is determined using the needle program in the EMBOSS software package, using the EDNAFULL scoring matrix and a gap opening penalty of 16, 14, 12, 10, 8, 6, or 4 and a gap extension penalty of 0.5, 1, 2, 3, 4, 5, or 6. Further preferred parameters to be used in conjunction for aligning two nucleic acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10).

Preferably, a variant of I-SceI as referred to herein includes those variants which are encoded by a nucleic acid which hybridizes specifically and, preferably, under stringent conditions, with a nucleic acid encoding the amino acid sequence shown in SEQ ID NO: 1. These stringent conditions are known to the skilled artisan and can be found in Current Protocols in Molecular Biology, John Wiley & Sons, N.Y. (1989), 6.3.1-6.3.6. Preferred stringent hybridization conditions are hybridization conditions in 6× sodium chloride/sodium citrate (=SSC) at approximately 45° C., followed by one or more washing steps in 0.2×SSC, 0.1% SDS at 50 to 65° C. The skilled artisan knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled artisan knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA from yeast, preferably, from *Saccharomyces cervisiae*, may be used.

Preferably, envisaged by the present invention are also shortened I-SceI polypeptides which differ from SEQ ID NO: 1 or its aforementioned variants in that between 5 and 9 C-terminal amino acids, preferably at least the 5, 6, 7, 8 or up to all 9 C-terminal amino acids, are deleted.

The term "second module" as used herein refers to a second structural and/or functional part of the polypeptide encoded by the polynucleotide of the invention. Said second module, preferably, comprises or essentially consists of at least a second DNA binding domain and a cleavage domain derived from a restriction endonuclease. A cleavage domain as referred to herein is capable of cleaving a DNA molecule at a specific DNA cleavage site. A specific DNA cleavage site as referred to in accordance with the present invention refers to a site which is recognized by the cleavage domain and cleaved between predefined nucleotides. In contrast, some endonucleases have a cleavage domain which cleaves the DNA at a certain position regardless of the nucleotides present at this position. A prototype endonuclease which exhibits such unspecific cleavage is FokI. The second module may also comprise, in addition to the second DNA binding domain and cleavage domain, further domains. Such further domains, preferably, can be DNA binding domains as well domain mediating interaction between two second modules, or other domains which mediate interaction with regulatory proteins or transport proteins, e.g., interaction domains for nuclear transport regulating proteins. It will be understood that, preferably, the said second DNA binding domain and/or the cleavage domain can also be comprised in the second module as a complete endonuclease protein, such as a naturally occurring restriction endonuclease or a genetically modified endonuclease. Moreover, it is well known that restriction endonucleases and, in particular, the type II restriction endonucleases said, bind to DNA—with very few exceptions—as a homodimer. Accordingly, a DNA binding domain and cleavage domains as referred to herein may be found as a consequence of the homodimerization of two restriction endonuclease subunits. Preferably, the specific DNA cleavage site and said DNA recognition site of the second DNA binding domain of the restriction endonuclease are identical. Also preferably, said second DNA binding domain and the cleavage domain comprised in the second module are derived from a restriction endonuclease which exhibits reduced DNA binding and/or reduced catalytic activity when compared to the wild type restriction endonuclease. Details of preferred DNA binding domains to be applied in accordance with the present invention are described elsewhere herein. Also preferably, envisaged in accordance with the present invention are second modules which have a reduced capability of forming homodimers in the absence of the DNA recognition site. In particular, it is envisaged that in a particular preferred embodiment, a functional homodimer of the polypeptide as referred to herein above is only formed when the two polypeptide monomers are recruited to the corresponding DNA recognition sites. Thereby, unspecific DNA binding can be prevented which may occur due to the formation of a homodimer as a consequence of binding of one monomer to its corresponding recognition site and subsequent dimerization of a second monomer resulting from protein-protein interactions between the monomers rather than specific DNA binding.

Preferred endonucleases from which the second DNA binding domain and the DNA cleavage domain comprised in the second module can be derived are type IIP restriction endonucleases (see Pingoud 2005, loc cit). The recognition sites in a DNA molecule recognized by the DNA binding domains of such endonucleases, in contrast to those of the aforementioned homing endonucleases, consist of at least four, at least six or up to eight contiguous nucleotides. Preferably, said recognition sites are palindromic. Moreover, preferably, the type IIP enzymes cleave the DNA within the DNA recognition site or immediately adjacent thereto. The said DNA recognition site is found rather frequently in a genome. Preferred type IIP restriction endonucleases as referred to herein are selected from the group consisting of: PvuII, EcoRV BamHI, BcnI, BfaSORF1835P, BfiI, BglI, BglII, BpuJI, Bse634I, BsoBI, BspD6I, BstYI, Cfr10I, EcI18kI, EcoO109I, EcoRI, EcoRII, EcoRV, EcoR124I, EcoR124II, HinP1I, HincII, HindIII, Hpy99I, Hpy188I, MspI, MunI, MvaI, NaeI, NgoMIV, NotI, OkrAI, PabI, PacI, PspGI, PvuII, Sau3AI, SdaI, SfiI, SgrAI, ThaI, VvuYORF266P, DdeI, Eco57I, HaeIII, HhaI, HindII, and NdeI. More preferably, said type IIP restriction endonucleases or the DNA binding and cleavage domains derived therefrom are modified as to show no or at least reduced star activity, a reduced DNA binding with respect to their DNA recognition site ($K_m$) and/or a reduced DNA cleavage activity ($k_{cat}$) of the cleavage domain. More preferably, it is envisaged that in one embodiment the type II restriction endonuclease or the domains derived therefrom have a reduced capability of forming homodimers in the absence of the DNA recognition site. Suitable restriction endonucleases or domains thereof for this purposes can be obtained, e.g., by random mutagenesis and subsequent testing for dimerization in the presence and absence of the DNA recognition site. Those variants which dimerize only in the presence but not in the absence of the DNA recognition site can be identified and used for the polypeptide encoded by the polynucleotide of the present invention.

Most preferably, the endonuclease envisaged in accordance with the present invention is PvuII or a genetically modified variant thereof and, thus, said second DNA binding domain and the cleavage domain comprised in the second module are derived from PvuII. More preferably, the said second DNA binding domain and the cleavage domain comprised in the second module are derived from PvuII or a variant thereof and comprise at least one of following modifications: substitution T46G, substitution H83A, substitution Y94F, substitution T46G in combination with H83A, substitution T46G in combination with Y94F or substitution T46G in combination with H83A and Y94F. The positions of the modifications referred to before are indicated for the wild type PvuII protein. However, it is to be understood that these positions will vary if modified variants of the PvuII protein are used. Nevertheless, it is envisaged that DNA binding domains from such variants, preferably, also comprise at least one of the modifications at a corresponding position in their amino acid sequences. The amino acid sequence of PvuII is well known in the art and described, e.g., in Athanasiadis 1990, Nucleic acid Res 18(21): 6434. Moreover, nucleic acid sequences encoding said PvuII amino acid sequences have also been described and can be derived from the amino acid sequence by the skilled artisan without further ado taking into account the degeneracy of the genetic code.

In a particular preferred embodiment, the PvuII wild type sequence referred to in accordance with the present invention has an amino acid sequence as shown in SEQ ID NO: 2 or is a variant thereof having an amino acid sequence which differs from SEQ ID NO: 2 by at least one amino acid substitution, deletion and/or addition.

Preferably, such a variant of PvuII has an amino acid sequence which is at least 70%, at least 80%, at least 90%, at least 95%, at least 98% or at least 99% identical with SEQ ID NO: 2 and, preferably, comprises a DNA binding domain having essentially the same DNA binding and cleavage properties as the DNA binding and cleavage domain of PvuII having SEQ ID NO: 2. How to determine said sequence identity is described elsewhere herein in detail.

Preferably, variants of PvuII as referred to herein include those variants which are encoded by a nucleic acid which hybridizes specifically and, preferably, under stringent conditions, with a nucleic acid encoding the amino acid sequence shown in SEQ ID NO: 2. Preferred stringent hybridization conditions are described elsewhere herein in detail. Alternatively, polynucleotide variants are obtainable by PCR-based techniques such as mixed oligonucleotide primer-based amplification of DNA, i.e. using degenerate primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA from bacteria and, preferably, *Proteus vulgaris*, may be used.

Within the polypeptide encoded by the polynucleotide of the present invention, the first module is separated from the second module by a linker. Said linker, preferably, is a flexible structure of sufficient length allowing the DNA binding domains comprised in the modules to interact with their DNA binding sites and allowing the DNA cleavage domain to cleave the DNA. Flexible linker structures to be used in the polypeptide encoded by the polynucleotide of the present invention, preferably, consist of five to twenty, more preferably, six to ten amino acids or more, i.e. at least six, at least seven, at least eight, at least nine or ten or more amino acids. Preferably, said linker has an amino acid sequence as shown in SEQ ID NO: 3 (ASRTTG) or SEQ ID NO: 4 (ASTKQLVKSG). Alternatively, the linker may have an amino acid sequence as in SEQ ID NO: 5 (ASGGSGSGSG) or SEQ ID NO: 6 (ASGDSGSDSG).

The polypeptide encoded by the polynucleotide of the invention shall functionally interact only with DNA comprising a DNA recognition site for the first DNA binding domain and the DNA recognition site for the second DNA binding domain. Accordingly, neither the first DNA binding domain nor the second DNA binding domain shall be, preferably, sufficient for allowing a functional interaction of the polypeptide encoded by the polynucleotide of the invention with DNA. A functional interaction as used herein refers to specific DNA binding to the DNA binding sites such that the cleavage domain can cleave at its specific DNA cleavage site upon binding. In order to be functional, the polypeptide according to the invention will form a homodimer comprising two polypeptide monomers as having the structure of the polypeptide of the invention. The second modules of the two polypeptides physically interact with each other. The second modules are then capable of binding to the second DNA recognition site in dimerized form. Thus, the polypeptide of the invention in its dimerized functional form recognizes a tripartite DNA recognition site which comprises the recognition site of the second DNA binding domain flanked by a recognition site for the first DNA binding domain at its 5' and its 3' ends. Upon specific binding to said tripartite DNA recognition site, the polypeptide via its DNA cleavage domain shall cleave the DNA within the said specific cleavage site or adjacent thereto. Preferably, said cleavage site and the second DNA binding site are identical. Thus, the DNA is cleaved at defined nucleotides within the cleavage site or adjacent thereto by the polypeptide according to the present invention.

A preferred polynucleotide of the present invention encodes a polypeptide that comprises (i) a first module comprising at least the DNA binding domain derived from I-SceI and, preferably, an inactive variant of I-SceI as specified above, (ii) a linker having SEQ ID NO: 3 or 4; and (iii) a second module comprising at least a second DNA binding domain and a cleavage domain derived from PvuII and, preferably, a PvuII variant as specified above wherein the DNA binding and cleavage domain are modified as to show no or at least reduced star activity, to have a reduced DNA binding with respect to their DNA recognition site and/or to exhibit reduced DNA cleavage by the cleavage domain. The polypeptide encoded by such a polynucleotide shall functionally interact only with DNA comprising a DNA recognition site for the first DNA binding domain of I-SceI and the DNA recognition site for the second DNA binding domain derived from PvuII. Since PvuII will form a homodimer in order to form an active enzyme, it will be understood that the DNA binding site recognized by the polypeptide is a tripartite DNA binding site comprising a PvuII DNA binding site flanked at the 5' and the 3' end by a I-SceI DNA binding site (I-SceI DNA recognition site-PvuII DNA recognition site-I-SceI DNA recognition site). Moreover, the polypeptide will cleave DNA within a specific DNA cleavage site upon binding, i.e. within defined positions and nucleotides of the PvuII binding site.

More preferably, the polynucleotide of the present invention encoding such a polypeptide comprises a nucleic acid sequence as shown in any one of SEQ ID NOs: 7 or 8 or which encodes a polypeptide comprising an amino acid sequence as shown in any one of SEQ ID NOs: 9 or 10. Variant polynucleotides having a nucleic acid sequence which differs from SEQ ID NOs: 7 or 8 or encoding an amino acid sequence which differs from SEQ ID NOs: 9 or 10 by at least one nucleotide or amino acid substitution, deletion and/or addition are also encompassed by the present invention. Preferably, such a variant has a nucleic acid sequence which is at least 70%, at least 80%, at least 90%, at least 95%, at least 98% or at least 99% identical with SEQ ID NOs: 7 or 8 or an amino acid sequence which is at least 70%, at least 80%, at least 90%, at least 95%, at least 98% or at least 99% identical with SEQ ID NOs: 9 or 10. Such variants, preferably, comprise the aforementioned first and second modules as well as the linker. How to determine said sequence identity is described elsewhere herein in detail. Also preferably, variants as referred to herein include those variants which are encoded by a nucleic acid which hybridizes specifically and, preferably, under stringent conditions, with a nucleic acid encoding the amino acid sequence shown in SEQ ID NO: 7 or 8 or to a nucleic acid encoding an amino acid sequence as shown in SEQ ID NOs: 9 or 10. Again, such variants, preferably, comprise the structural characteristics of the aforementioned first and second modules as well as the linker.

Advantageously, the present invention provides a polynucleotide which encodes a polypeptide capable of specifically recognizing an artificially composed tripartite DNA recognition sequence and which is capable of cleaving a DNA comprising such tripartite DNA recognition sequence within a specific DNA cleavage site, i.e. at a defined position between predefined nucleotides. Since the tripartite DNA recognition sequence is a rather large sequence, it will presumably occur only rarely within a natural occurring genome. Preferably, the said tripartite DNA recognition site occurs statistically less than once per genome. As a consequence, the polypeptide according to the present invention shall cleave the genome only rarely and, preferably, once, i.e. at the tripartite DNA recognition site. Thereby, the polypeptide can facilitate integration of heterologous DNA, e.g., a transgene, at a certain locus within the genomic DNA that can be easily identified after the integration took place. Moreover, homologous recombination events can be facilitated as well. Thanks to the present invention, the generation of transgenic organisms, such as transgenic microorganisms, transgenic plants or transgenic animals, will be significantly improved. The polypeptide of the present invention, however, can also be used as a tool for mere DNA cleavage, i.e. as a rare cutting endonuclease specific for the aforementioned artificial tripartite DNA recognition site. Such a rare cutting endonuclease can, of course, be applied for all conventional cloning approaches. The polynucleotide of the present invention encodes a polypeptide which has an improved specificity compared to zinc finger nucleases or TALe nucleases as well as so-called artificial meganucleases since it recognizes an extended tripartite DNA recognition site as described above. Moreover, it has been found that even blunt end cutters, such as PvuII, can be used for generating the polypeptide of the present invention. This is somewhat surprising since it was reported previously that blunt ends introduced into genomic DNA by blunt end cutting endonucleases such as PvuII may be poor substrates for the repair system in some organisms (Westmoreland 2010, DNA Repair 9: 617-626).

The explanations and definitions given for the terms above apply mutatis mutandis for the following embodiments of the invention.

The present invention also relates to a vector comprising the polynucleotide of the present invention.

The term "vector" as used herein encompasses phage, plasmid, viral or retroviral vectors as well as artificial chromosomes, such as bacterial or yeast artificial chromosomes. The vector encompassing the polynucleotides of the present invention, preferably, further comprises selectable markers for propagation and/or selection in a host. Vectors can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual, 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, Agrobacterium protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host cells.

Suitable cloning vectors are generally known to the skilled worker. In particular, they include vectors which can replicate in microbial systems. These vectors, preferably, ensure efficient cloning in bacteria, yeasts or fungi.

Preferably, in the vector of the invention the polynucleotide is operatively linked to an expression control sequences allowing expression in prokaryotic or eukaryotic host cells or isolated fractions thereof. Thus, preferably, the vector of the present invention is an expression vector. Expression of the polynucleotide comprises transcription of the polynucleotide into a translatable mRNA. Regulatory elements ensuring expression in host cells are well known in the art. Preferably, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in E. coli, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide.

Preferably, the expression of proteins in prokaryotes, preferably, involves the use of vectors comprising constitutive or inducible promoters which govern the expression of fusion or nonfusion proteins. Typical fusion expression vectors are, inter alia, pGEX (GE Healthcare, Piscataway, N.J.; Smith 1988, Gene 67:31-40), pMAL (New England Biolabs, Ipswich, Mass.) and pRIT5 (GE Healthcare, Piscataway, N.J.), where glutathione S-transferase (GST), maltose-E-binding protein and protein A, respectively, is fused with the recombinant target protein. Examples of suitable inducible nonfusion E. coli expression vectors are, inter alia, pTrc (Amann 1988, Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter. Other vectors which are suitable for prokaryotic organisms are known to the skilled worker, these vectors are, for example in E. coli pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCI, in Streptomyces pIJ101, pIJ364, pIJ702 or pIJ361, in Bacillus pUB110, pC194 or pBD214, in Corynebacterium pSA77 or pAJ667.

Also preferably encompassed herein are yeast expression vectors. Examples for vectors for expression in the yeast S. cerevisiae comprise pYeDesaturasec1 (Baldari 1987, EMBO J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, the polynucleotides according to the invention can also be expressed in insect cells using Baculovirus expression vectors. Baculovirus vectors which are available for the expression of proteins in cultured insect cells (for example Sf9 cells) comprise the pAc series (Smith 1983, Mol. Cell. Biol. 3:2156-2165) and the pVL series (Lucklow 1989, Virology 170:31-39).

Suitable expression vectors for eukaryotic cells which are also preferably encompassed by the present invention are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Expression vectors can also be derived from viruses such as retroviruses, vaccinia virus, adeno-associated virus, herpes viruses, or bovine papilloma virus, may be used for delivery of the polynucleotide or vector of the invention into a targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Preferred plant expression vectors comprise those which are described in detail in: Becker 1992, Plant Mol. Biol. 20:1195-1197; and Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette preferably comprises expression control sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen 1984, EMBO J. 3: 835 ff), which is known as octopine synthase, or functional equivalents thereof, but all other terminators which are functionally active in plants are also suitable. Since plant gene expression is very often not limited to the transcriptional level, a plant expression cassette preferably comprises other sequences which are linked operatively, such as translation enhancers, for example the overdrive sequence, which comprises the tobacco mosaic virus 5'-untranslated leader sequence, which increases the protein/RNA ratio (Gallie 1987, Nucl. Acids Research 15:8693-8711). As described above, plant gene expression must be linked operably with a suitable promoter which triggers gene expression with the correct timing or in a cell- or tissue-specific manner. Utilizable promoters are constitutive promoters (Benfey 1989, EMBO J. 8: 2195-2202), such as those which are derived from plant viruses, such as 35S CAMV (Franck 1980, Cell 21: 285-294), 19S CaMV (see also U.S. Pat. No. 5,352,605 and WO 84/02913), or plant promoters, such as the promoter of the small Rubisco subunit, which is described in U.S. Pat. No. 4,962, 028. Other preferred sequences for use in operable linkage in plant gene expression cassettes are targeting sequences, which are required for steering the gene product into its corresponding cell compartment (see a review in Kermode 1996, Crit. Rev. Plant Sci. 15, 4: 285-423 and references cited therein), for example into the vacuole, into the nucleus, all types of plastids, such as amyloplasts, chloroplasts, chromoplasts, the extracellular space, the mitochondria, the endoplasmic reticulum, oil bodies, peroxisomes and other compartments of plant cells.

Gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO95/19443), a tetracycline-inducible promoter (Gatz 1992, Plant J. 2, 397-404) and an ethanol-inducible promoter.

The present invention contemplates a non-human organism comprising the polynucleotide or the vector of the present invention.

The term "non-human organism" as used herein relates to any organism except human beings. Accordingly, the non-human organism, preferably, is a microorganism, a plant, plant part or isolated cell thereof, or an animal, animal tissue or isolated cell thereof. Moreover, eukaryotic or bacterial host cells are encompassed as non-human organisms as well. The non-human organism may comprise the polynucleotide of the invention or the vector of the invention for the purpose of DNA propagation as well as for the purpose of expressing the polypeptide according to this invention or both. The polynucleotide or vector may be present integrated into the genome of the host or present in an episomal form. Further preferred non-human organisms according to the present invention are described in the following.

Preferred microorganisms are prokaryotic and eukaryotic microorganisms and, in particular, are selected from bacteria, fungi, yeast or cell culture cells from any one of the non-human animals or plants specified below.

Preferred non-human animals include mammals, birds, reptiles, fish, nematodes, and insects. More preferably, the non-human animal is a mammal and, in particular, a rat, a mouse, a rabbit, a dog, a cat or a farming animal, such as a pig, a horse, a sheep or a cow.

Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, Anacardiaceae such as the genera *Pistacia, Mangifera, Anacardium*, Asteraceae, such as the genera *Calendula, Carthamus, Centaurea, Cichorium, Cynara, Helianthus, Lactuca, Locusta, Tagetes, Valeriana*, Apiaceae, such as the genus *Daucus*, Betulaceae, such as the genus *Corylus*, Boraginaceae, such as the genus *Borago*, Brassicaceae, such as the genera *Brassica, Melanosinapis, Sinapis, Arabadopsis*, Bromeliaceae, such as the genera *Ananas, Bromelia*, Caricaceae, such as the genus *Carica*, Cannabaceae, such as the genus *Cannabis*, Convolvulaceae, such as the genera *Ipomea, Convolvulus*, Chenopodiaceae, such as the genus *Beta*, Crypthecodiniaceae, such as the genus *Crypthecodinium*, Cucurbitaceae, such as the genus *Cucurbita*, Cymbellaceae such as the genera *Amphora, Cymbella, Okedenia, Phaeodactylum, Reimeria*, Ditrichaceae such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, Elaeagnaceae such as the genus *Elaeagnus*, Ericaceae such as the genus *Kalmia*, Euphorbiaceae such as the genera *Manihot, Janipha, Jatropha, Ricinus*, Fabaceae such as the genera *Pisum, Albizia, Cathormion, Feuillea, Inga, Pithecolobium, Acacia, Mimosa, Medicago, Glycine, Dolichos, Phaseolus, Soja*, Funariaceae such as the genera *Aphanorrhegma, Entosthodon, Funaria, Physcomitrella, Physcomitrium*, Geraniaceae, such as the genera *Pelargonium, Cocos, Oleum*, Gramineae, such as the genus *Saccharum*, Juglandaceae, such as the genera *Juglans, Wallia*, Lauraceae, such as the genera *Persea, Laurus*, Leguminosae, such as the genus *Arachis*, Linaceae, such as the genera *Linum, Adenolinum*, Lythrarieae, such as the genus *Punica*, Malvaceae, such as the genus *Gossypium*, Marchantiaceae, such as the genus *Marchantia*, Musaceae, such as the genus *Musa*, Onagraceae, such as the genera *Camissonia, Oenothera*, Palmae, such as the genus *Elacis*, Papaveraceae, such as the genus *Papaver*, Pedaliaceae, such as the genus *Sesamum*, Piperaceae, such as the genera *Piper, Artanthe, Peperomia, Steffensia*, Poaceae, such as the genera *Hordeum, Secale, Avena, Sorghum, Andropogon, Holcus, Panicum, Oryza, Zea* (maize), *Triticum*, Porphyridiaceae, such as the genera *Chroothece, Flintiella, Petrovanella, Porphyridium, Rhodella, Rhodosorus, Vanhoeffenia*, Proteaceae, such as the genus *Macadamia*, Prasinophyceae such as the genera *Nephroselmis, Prasinococcus, Scherffelia, Tetraselmis, Mantoniella, Ostreococcus*, Rubiaceae such as the genus *Cofea*, Scrophulariaceae such as the genus *Verbascum*, Solanaceae such as the genera *Capsicum*, *Nicotiana*, *Solanum*, *Lycopersicon*, Sterculiaceae, such as the genus *Theobroma*, or Theaceae, such as the genus *Camellia*.

More preferably, the plant is selected from the group of plant families Asteraceae, Brassicaceae, Chenopodiaceae, Euphorbiaceae, Gramineae, Leguminosae, and Malvaceae.

Especially preferred are for example the genera and species *Brassica napus*, *Brassica rapa* ssp., *Sinapis arvensis*, *Brassica juncea*, *Brassica juncea* var. *juncea*, *Brassica juncea* var. *crispifolia*, *Brassica juncea* var. *foliosa*, *Brassica nigra*, *Brassica sinapioides*, *Melanosinapis communis*, *Brassica oleracea*, *Arabidopsis thaliana*, *Beta vulgaris*, *Beta vulgaris* var. *altissima*, *Beta vulgaris* var. *Vulgaris*, *Beta maritima*, *Beta vulgaris* var. *perennis*, *Beta vulgaris* var. *conditiva* or *Beta vulgaris* var. *esculenta*, *Phaeodactylum tricornutum*, *Pisum sativum*, *Pisum arvense*, *Pisum humile*, *Albizia berteriana*, *Albizia julibrissin*, *Albizia lebbeck*, *Acacia berteriana*, *Acacia littoralis*, *Albizia berteriana*, *Albizzia berteriana*, *Cathormion berteriana*, *Feuillea berteriana*, *Inga fragrans*, *Pithecellobium berterianum*, *Pithecellobium fragrans*, *Pithecolobium berterianum*, *Pseudalbizzia berteriana*, *Acacia julibrissin*, *Acacia nemu*, *Albizia nemu*, *Feuilleea julibrissin*, *Mimosa julibrissin*, *Mimosa speciosa*, *Sericanrda julibrissin*, *Acacia lebbeck*, *Acacia macrophylla*, *Albizia lebbek*, *Feuilleea lebbeck*, *Mimosa lebbeck*, *Mimosa speciosa*, *Medicago sativa*, *Medicago falcata*, *Medicago varia*, *Glycine max Dolichos soja*, *Glycine gracilis*, *Glycine hispida*, *Phaseolus max*, *Soja hispida* or *Soja max*, *Hordeum vulgare*, *Hordeum jubatum*, *Hordeum murinum*, *Hordeum secalinum*, *Hordeum distichon*, *Hordeum aegiceras*, *Hordeum hexastichon*, *Hordeum hexastichum*, *Hordeum irregulare*, *Hordeum sativum*, *Hordeum secalinum*, *Secale cereale*, *Avena sativa*, *Avena fatua*, *Avena byzantina*, *Avena fatua* var. *sativa*, *Avena hybrida*, *Sorghum bicolor*, *Sorghum halepense*, *Sorghum saccharatum*, *Sorghum vulgare*, *Andropogon drummondii*, *Holcus bicolor*, *Holcus sorghum*, *Sorghum aethiopicum*, *Sorghum arundinaceum*, *Sorghum caffrorum*, *Sorghum cernuum*, *Sorghum dochna*, *Sorghum drummondii*, *Sorghum durra*, *Sorghum guineense*, *Sorghum lanceolatum*, *Sorghum nervosum*, *Sorghum saccharatum*, *Sorghum subglabrescens*, *Sorghum verticilliflorum*, *Sorghum vulgare*, *Holcus halepensis*, *Sorghum miliaceum*, *Panicum militaceum*, *Oryza sativa*, *Oryza latifolia*, *Zea mays*, *Triticum aestivum*, *Triticum durum*, *Triticum turgidum*, *Triticum hybernum*, *Triticum macha*, *Triticum sativum* or *Triticum vulgare*, *Capsicum annuum*, *Capsicum annuum* var. *glabriusculum*, *Capsicum frutescens*, *Capsicum annuum*, *Nicotiana tabacum*, *Nicotiana alata*, *Nicotiana attenuata*, *Nicotiana glauca*, *Nicotiana langsdorffii*, *Nicotiana obtusifolia*, *Nicotiana quadrivalvis*, *Nicotiana repanda*, *Nicotiana rustica*, *Nicotiana sylvestris*, *Solanum tuberosum*, *Solanum melongena*, *Lycopersicon esculentum*, *Lycopersicon lycopersicum*, *Lycopersicon pyriforme*, *Solanum integrifolium* or *Solanum lycopersicum*.

The most preferred plant species are *Brassica napus*, *Brassica rapa*, *Brassica oleracea*, *Beta vulgaris*, *Medicago sativa*, *Glycine max Dolichos soja*, *Hordeum vulgare*, *Secale cereale*, *Avena sativa*, *Sorghum bicolor*, *Sorghum halepense*, *Sorghum saccharatum*, *Sorghum vulgare*, *Panicum militaceum*, *Oryza sativa*, *Zea mays*, *Triticum aestivum*, *Triticum durum*, *Solanum tuberosum*, *Lycopersicon esculentum*, and *Gossypium hirsutum*.

Transgenic plants may be obtained by transformation techniques as elsewhere in this specification. Preferably, transgenic plants can be obtained by T DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Preferred mosses to be used as non-human transgenic organisms according to the present invention are *Physcomitrella* or *Ceratodon*. Preferred algae to be used as non-human transgenic organisms according to the present invention are *Isochrysis*, *Mantoniella*, *Ostreococcus* or *Crypthecodinium*, and algae/diatoms such as *Phaeodactylum* or *Thraustochytrium*.

The present invention relates to a polypeptide encoded by the polynucleotide of the present invention.

The term "polypeptide" as used herein encompasses isolated or essentially purified polypeptides being essentially free of other components. However, the term also encompasses polypeptide preparations comprising the polypeptide of the present invention and other proteins in addition. A polypeptide as used herein may by a chemically modified polypeptide. Said modifications may be artificial modifications or naturally occurring modifications. The polypeptide of the present invention shall have the activities referred to above. It can be manufactured by chemical synthesis or recombinant molecular biology techniques well known for the skilled artisan. Preferably, such a method of manufacturing the polypeptide of the invention comprises (a) culturing the host cell of the present invention described elsewhere herein in more detail and (b) obtaining from the said host cell the polypeptide of the present invention. In an aspect of this method, the polypeptide can be obtained by conventional purification techniques from a lysate of the host cell including affinity chromatography, ion exchange chromatography, size exclusion chromatography, hydrophobic interaction chromatography and/or preparative gel electrophoresis. Details on the manufacture and testing for the desired activities are also found in the accompanying Examples below.

As indicated elsewhere herein, the polypeptide of the present invention can be applied in various genetic engineering procedures. Thus, contemplated in accordance with the present invention is, inter alia, the use of the polypeptide of the invention in a non-human organism and, preferably, a microorganism or plant, for integrating a heterologous nucleic acid of interest into a target nucleic acid molecule, preferably, into a genomic target DNA, such as a chromosome. Also contemplated is the use of the polypeptide of the invention in a non-human organism and, preferably, a microorganism or plant, for facilitating the integration of a heterologous nucleic acid of interest into a target nucleic acid molecule, preferably, into a genomic target DNA, such as a chromosome. Preferably, the integration of the nucleic acid of interest will occur at the site of the tripartite DNA recognition site in the target nucleic acid molecule. Accordingly, the polypeptide of the present invention can be, preferably, used for targeted transgenesis (gene insertion), gene knock-out approaches (gene inactivation) or homologous replacement or knock-in approaches (gene replacement). In particular, the polypeptide of the present invention can also be used for the removal or inactivation of nucleic acids of interest from a genome, such as for the removal of marker genes used for the selection of transgenic non-human organisms after the said selection has been carried out. Furthermore, the polypeptide of the present invention by allowing targeted transgenesis at a predetermined locus allows for controlling the integration site and the copy number of the transgenes to be integrated.

Encompassed by the present invention is a method for introducing a nucleic acid of interest into a genome of a non-human organism comprising:

a) introducing into a non-human organism a nucleic acid of interest to be introduced into the genome of the said organism
b) expressing the polypeptide of the present invention in said organism; and
c) cultivating said organism under conditions allowing said polypeptide to cleave the genome and allowing the nucleic acid of interest to become introduced into the genome.

In the method of the present invention, a nucleic acid of interest, which shall be incorporated into the genome of a non-human organism as specified elsewhere herein, is introduced into the said organism. The introduction of the nucleic acid of interest can be achieved by various transfection or transformation techniques as referred to elsewhere herein in more detail. A nucleic acid of interest as referred to herein encompasses nucleic acids which shall be expressed by the non-human organisms, such as nucleic acids encoding proteins or RNAs, the production of which is envisaged, or nucleic acids which shall be used to disrupt genes in the genome or shall be incorporated for any other reason into the organisms genome.

The non-human organism according to the method of the present invention shall express the polypeptide of the present invention. This can be achieved, preferably, by generating a transgenic non-human organism which comprises as a transgene either stably or transiently integrated the polynucleotide of the present invention in an expressible form. To this end, the polynucleotide may be, preferably, transformed or transfected into the organism comprised in an expression vector and, preferably, an expression vector of the invention as specified above. Moreover, the transgenic non-human organism to be applied in the method of the present invention is selected from the group consisting of: a microorganism, a plant, plant part or isolated cell thereof, or an animal tissue or isolated cell thereof and, most preferably, is one of the non-human transgenic organisms of the invention as specified explicitly elsewhere herein.

It will be understood that in the non-human transgenic organism to be used in the method of the invention, the polypeptide of the invention is present in a biologically active form, i.e. is capable of binding to the tripartite DNA recognition site and is capable of cleaving the DNA upon binding within its DNA cleavage site. DNA binding and cleavage by the polynucleotide of the invention can be achieved by culturing the non-human transgenic organism for a time and under conditions which allow for the said DNA binding and cleavage. Moreover, the non-human organism shall be cultured under conditions allowing for the integration of the nucleic acid of interest into the cleaved genomic DNA. Suitable conditions can be applied by the skilled person without further ado and, in most cases, the integration of the nucleic acid of interest results from or is facilitated by endogenous DNA repair processes which are triggered by the DNA cleavage elicited by the polypeptide of the present invention in the genome of the non-human organism. Preferred conditions which allow for DNA binding and cleavage are described in the accompanying Examples below in more detail or can be derived from any one of WO2003/080809, WO2000/46386, WO2009/006297, WO2006/074956, WO2006/134496, WO2007/148964, and/or WO2009/130695.

The present invention, finally, relates to a nucleic acid molecule comprising the tripartite DNA recognition site of the polypeptide of the present invention.

Preferably, the said nucleic acid molecule is a nucleic acid of interest for integration into a genome comprised, e.g., by a vector. Alternatively, the said nucleic acid molecule can be comprised in a genome into which the nucleic acid of interest as referred to above shall be integrated. The tripartite DNA recognition site comprised in the aforementioned nucleic acid molecule is, preferably, a DNA recognition site comprising the recognition site of the first DNA binding domain linked to the recognition site of the second DNA binding domain linked to the recognition site of the first DNA binding domain.

In a preferred embodiment, the nucleic acid molecule comprising the tripartite DNA recognition site of the polypeptide of the present invention comprises in 5' to 3' direction:
 i. a DNA recognition site of a homing endonuclease,
 ii. a first nucleic acid linker,
 iii. a DNA recognition site of a restriction endonuclease,
 iv. a second nucleic acid linker, and
 v. the reverse complement sequence of a DNA recognition site of a homing endonuclease.

Preferred homing endonucleases as well as preferred restriction endonucleases are described elsewhere herein. Preferably, the homing endonuclease in (i) and (v) is a LAGLIDADG-family homing endonuclease or a variant thereof. More preferably, it is a I-SceI homing endonuclease or of a variant thereof. Preferably, the restriction endonuclease in (v) is a type IIP restriction endonucleases. Most preferably, it is PvuII.

Thus, in a further preferred embodiment, the nucleic acid molecule comprising the tripartite DNA recognition site comprises in 5' to 3' direction:
 i. a DNA recognition site of I-SceI,
 ii. a first nucleic acid linker,
 iii. a DNA recognition site of PvuII,
 iv. a second nucleic acid linker, and
 vi. the reverse complement sequence of a DNA recognition site of I-SceI.

A preferred DNA recognition site of I-SceI is represented by bases 1 to 18 of SEQ ID NO: 11. A preferred reverse complement sequence of a DNA recognition site of I-SceI is represented by bases 37 to 54 of SEQ ID NO: 11. The DNA recognition site of PvuII is represented by bases 25 to 30 of SEQ ID NO: 11 (cagctg).

It is known homing endonucleases, including I-SceI, can tolerate small deviations (degenerations) of the nucleotide sequence of their recognition sites which nevertheless make recognition and cleavage by the particular homing endonuclease possible. Thus, tripartite DNA recognition sites comprising 1, 2, 3 or 4 nucleotide exchanges in one or both homing endonuclease recognition sites are also included here.

The said recognition sites shall be linked via a nucleic acid linker sequences comprising a number of nucleotides sufficient in length as to allow the specific binding of the homodimer of the polypeptide of the present invention (as set forth in ii. and iv.). The length of the nucleic acid linkers will depend on the size of the polypeptide of the present invention and, in particular, the length of the linker in the polypeptide of the invention. Preferably, the nucleic acid linker encompass between 1 to 20 in length, more preferably 4 to 8 nucleotides in length, even more preferably between 5 and 7 nucleotides in length, and most preferably 6 nucleotides in length. The nucleotides of the linker nucleic acids can be either identical or differ from each other. Preferably, the linker nucleic acid does, however, not interfere or influence DNA binding of the homodimer. Whether a nucleic acid linker influences or interferes with the DNA binding can be determined by well known techniques.

In one embodiment, the tripartite DNA recognition site comprises a nucleic acid sequence of:
a) a nucleic acid sequence as described by SEQ ID NO: 11, 12, or 13,
b) a nucleic acid sequence differing by 1, 2, 3 or 4 bases from a nucleic acid sequence as described by SEQ ID NO: 11, 12, or 13, those differences being located at bases 1 to 18 of a sequence as described by SEQ ID NO: 11, 12, or 13,
c) a nucleic acid sequence differing by 1, 2, 3 or 4 bases from a nucleic acid sequence as described by SEQ ID NO: 11, 12, or 13, those differences being located at bases 37 to 54 of a sequence as described by SEQ ID NO: 11, 12, or 13,
d) a nucleic acid sequence differing by 2, 3, 4, 5, 6, 7, or 8 bases from a nucleic acid sequence as described by SEQ ID NO: 11, 12, or 13, those differences being located at bases 1 to 18 and at bases 37 to 54 of a sequence as described by SEQ ID NO: 11, 12, or 13, but not having more than 4 differing bases located at bases 1 to 18 and not more than 4 differing bases located at bases 37 to 54.

Preferably, the tripartite DNA recognition site comprises a nucleic acid sequence as shown in SEQ ID NO: 11, 12, or 13.

Advantageously, the present invention provides for an artificial tripartite DNA recognition site which shall be not endogenously present in a genome. Accordingly, integration of heterologous DNA can be governed more precisely in non-human organisms carrying said tripartite DNA recognition site as a result of DNA recombination techniques, e.g., homologous recombination, at a certain desired locus.

Thus, contemplated in accordance with the present invention is, inter alia, the use of the nucleic acid molecule comprising the tripartite DNA recognition site of the polypeptide of the present invention in a non-human organism and, preferably, a microorganism or plant, for integration into a target nucleic acid molecule, preferably, into a genomic target DNA, such as a chromosome. Accordingly, the present invention also relates to a non-human organism comprising a nucleic acid molecule comprising the tripartite DNA recognition site. Preferably, the nucleic acid molecule will also govern the integration of a nucleic acid molecule in the target nucleic acid molecule. Accordingly, the said nucleic acid molecule of the present invention can be, preferably, used for targeted transgenesis (gene insertion), gene knock-out approaches (gene inactivation) or homologous replacement or knock-in approaches (gene replacement). In particular, the nucleic acid molecule can also be used for the removal or inactivation of nucleic acids of interest from a genome, such as for the removal of marker genes used for the selection of transgenic non-human organisms after the said selection has been carried out. Furthermore, the nucleic acid molecule allows for targeted transgenesis at a predetermined locus comprising it and, thus for controlling the integration site and the copy number of the transgenes to be integrated.

It will be understood that the present invention, consequently, also contemplates a vector comprising the aforementioned nucleic acid molecule as well as a non-human organism comprising the said nucleic acid molecule.

Furthermore, preferably, the said nucleic acid molecule is applied in the method of the invention and further comprises in addition to the tripartite DNA recognition site the nucleic acid of interest to be integrate into the genome.

The definitions and explanations made for the vector, non-human organism and method above apply mutatis mutandis.

The present invention further relates to a non-human organism comprising the nucleic acid molecule comprising the tripartite DNA recognition site as described above and polynucleotide encoding the polypeptide of the present invention. Preferably said organism is a microorganism, a plant, or an animal. Preferably, the plant is transformed with said nucleic acid molecule and/or said polynucleotide encoding the polypeptide of the present invention.

All references cited throughout this specification are herewith incorporated by reference with respect to their specific disclosure contents discussed above and with respect to their entire disclosure contents.

FIGURES

Figure 5:
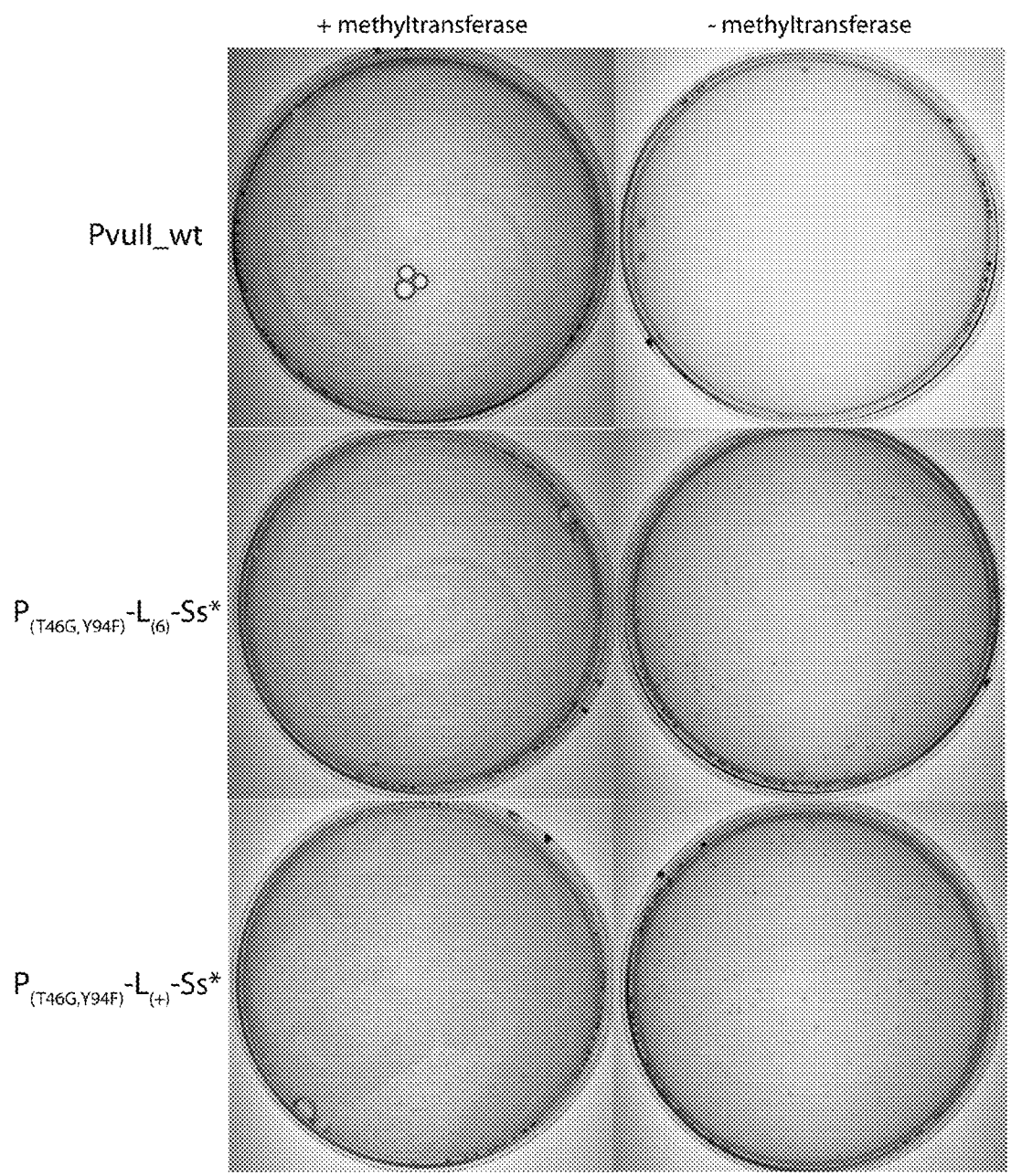

FIG. 5 shows an in vivo analysis for fusion protein activity. E. coli cells were transformed with a plasmid coding for the companion methyltransferase of PvuII. Either a plasmid encoding wild type PvuII, the L(6) fusion protein or the L(+) fusion protein was cotransformed. The fusion protein showed surviving colonies in the absence of methyltransferase demonstrating that the fusion protein does not attack unmethylated (i.e. unprotected) PvuII sites.

Figure 6:
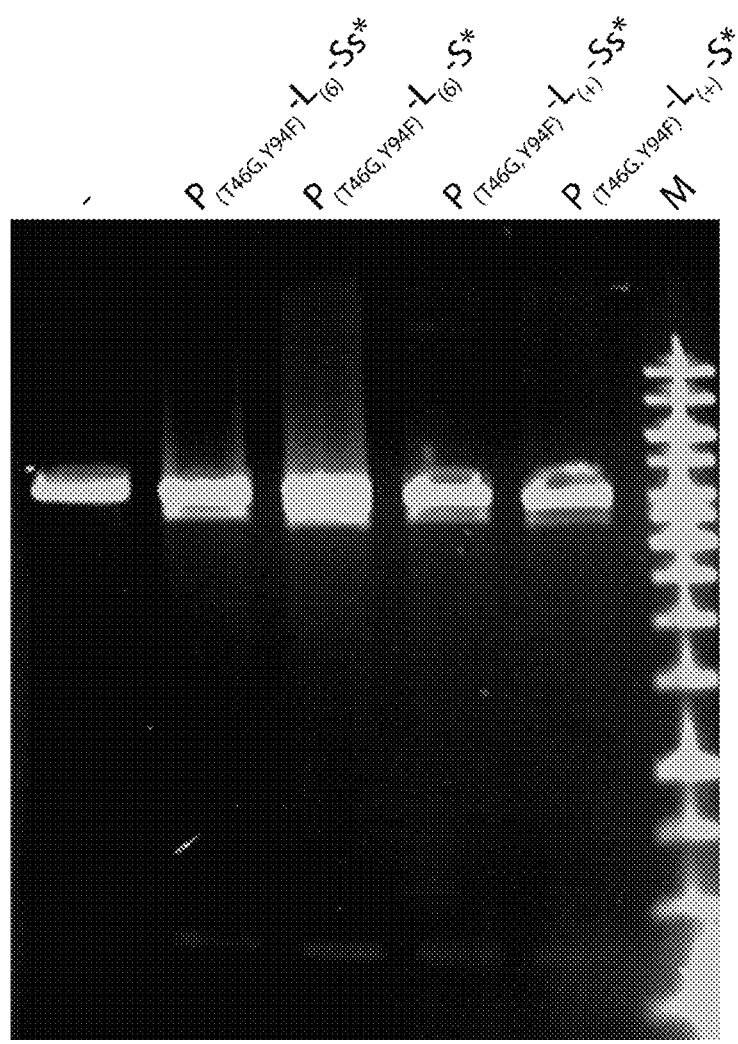

FIG. 6 shows an agarose gel analysis for determining the activity of shortened variants of the L(6) (SEQ ID NO: 9) and L(+) (SEQ ID NO: 10) fusion proteins. No difference was observed.

The following sequences referred to herein are shown in the accompanying sequence listing:
SEQ ID NO: 1: amino acid sequence of I-SceI;
SEQ ID NO: 2: amino acid sequence of PvuII;
SEQ ID NO: 3: Linker ASRTTG
SEQ ID NO: 4: Linker ASTKQLVKSG
SEQ ID NO: 5: Linker ASGGSGSGSG
SEQ ID NO: 6: Linker ASGDSGSDSG
SEQ ID NO: 7: nucleic acid sequence encoding fusion protein $P_{(T46G, Y94F)}$-$L_{(6)}$-Ss*;
SEQ ID NO: 8: nucleic acid sequence encoding fusion protein $P_{(T46G, Y94F)}$-$L_{(+)}$-Ss*;
SEQ ID No: 9: amino acid sequence of fusion protein $P_{(T46G, Y94F)}$-$L_{(6)}$-Ss*;
SEQ ID NO: 10: amino acid sequence of fusion protein $P_{(T46G, Y94F)}$-$L_{(+)}$-Ss*;

SEQ ID NO: 11: nucleic acid sequence for the tripartite DNA recognition site of the aforementioned fusion proteins: TAGGGATAACAGGGTAATGGTACTCAGCTGAT-TCATATTACCCTGTTATCCCTA.

SEQ ID NO: 12: nucleic acid sequence for the tripartite DNA recognition site of the aforementioned fusion proteins: TAGGGATAACAGGGTAATATGAATCAGCTGAGTAC-CATTACCCTGTTATCCCTA SEQ ID NO: 13: nucleic acid sequence for the tripartite DNA recognition site of the aforementioned fusion proteins: TAGGGATAACAGGGTAATNNNNNNCAGCT-GNNNNNNATTACCCTGTTATCCCTA,
wherein n can be A, T, C or G

EXAMPLES

The following Examples illustrate the invention and shall not, whatsoever, be construed as limiting the scope.

Example 1

Cloning of Different Fusion Proteins of I-SceI and PvuII

The PvuII-I-SceI fusion enzyme was created by fusing PvuII via its C-terminus to the N-terminus of a catalytically inactive variant of I-SceI (Gruen 2002, Nucleic Acids Res; 30(7):e29.) which was truncated at the C-terminus (corresponding to the co-crystal structure, Moure 2003, J. Mol. Biol. 334 (4) 685-95). For this the genes coding for PvuII was connected via its C-terminal His$_6$-tag to the gene coding for I-SceI$_{(D44S)}$ΔC9 and cloned into the vector pASK-IBA63b-plus (IBA) coding for a C-terminal Strep-tag. For further improvement the two active site residues (D44 and D145) of I-SceI were mutated according to Lippow 2009, Nucleic Acid Res 37(9): 3061-3073 via PCR-based directed mutagenesis (Kirsch 1998, Nucleic Acids Res. 26 (7) 1848-50). The resulting variants were later on called S* (I-SceI_D44N, D145A) and Ss* (I-SceIΔC9_D44N, D145A). The mutagenesis of certain residues of PvuII was performed in the same way for the fusion enzymes. To have a building block like architecture for the linker region between the genes for PvuII and I-SceI three restriction enzyme sites (NheI, BsiWI, AgeI) were introduced between these two gene instead of the His6-tag (L$_{(H)}$) leading to L$_{(6)}$ (SEQ ID No: 3). By cleaving the resulting vector with NheI and AgeI the linker L$_{(N)}$ (SEQ ID NO: 5), L$_{(+)}$ (SEQ ID NO: 4) and L$_{(-)}$ (SEQ ID NO: 6) having complementary ends could be cloned into these sites.

Example 2

Figure 1:
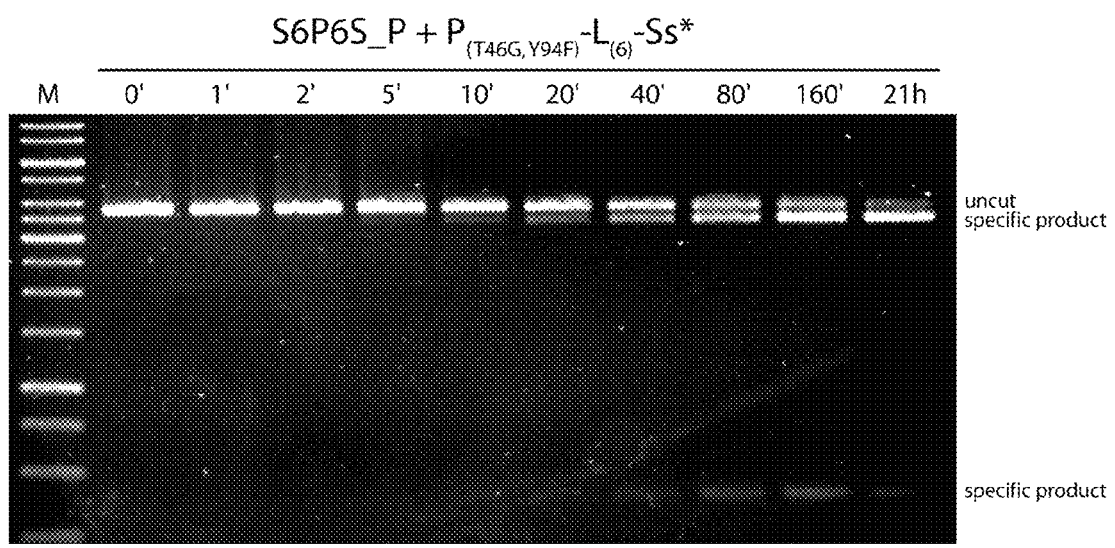
FIG. 1 shows an agarose gel analysis for determining cleavage products of the L(6) (SEQ ID NO: 9) variants of the polypeptide of the present invention at different time points after beginning of the incubation. The kinetic analysis revealed no cleavage at unspecific sites even after 21 hours of digestion.

Functional Characterization of Different Fusion Proteins 8 nM linearized plasmid DNA containing the tripartite site (S6P6S) and an additional unaddressed PvuII-site were incubated with 8 nM of the L(6) variant of the fusion enzyme (SEQ ID NO: 9) in optimized KG Buffer (100 mM potassium glutamate, 25 mM Tris-acetate, 0.8 mM Mg-acetate, 100 mM KCl, 500 µM 2-mercaptoethanol, 10 µg/ml BSA). This buffer is used for all further experiments as well. After certain time points a sample of the cleavage reaction was withdrawn, the reaction stopped by adding loading buffer and analyzed on agarose gel. The results are shown in FIG. 1.

Figure 2:
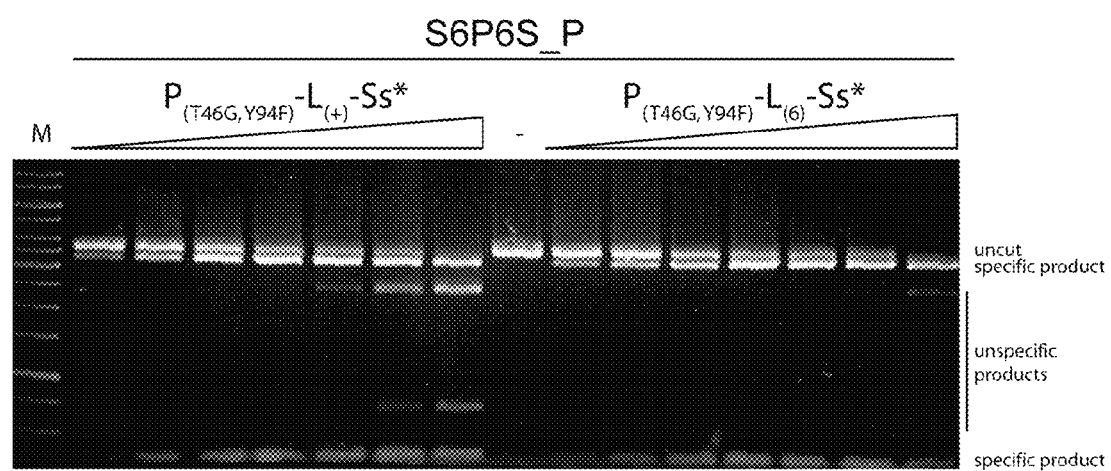
FIG. 2 shows an agarose gel analysis for determining cleavage products of the L(6) (SEQ ID NO: 9) and L(+) (SEQ ID NO: 10). variants of the polypeptide of the present invention at various different concentrations. The enzyme titration revealed unspecific cleavage only at a concentration of 8-32× molar excess of enzyme over DNA for the L(6) variant.
Figure 2:
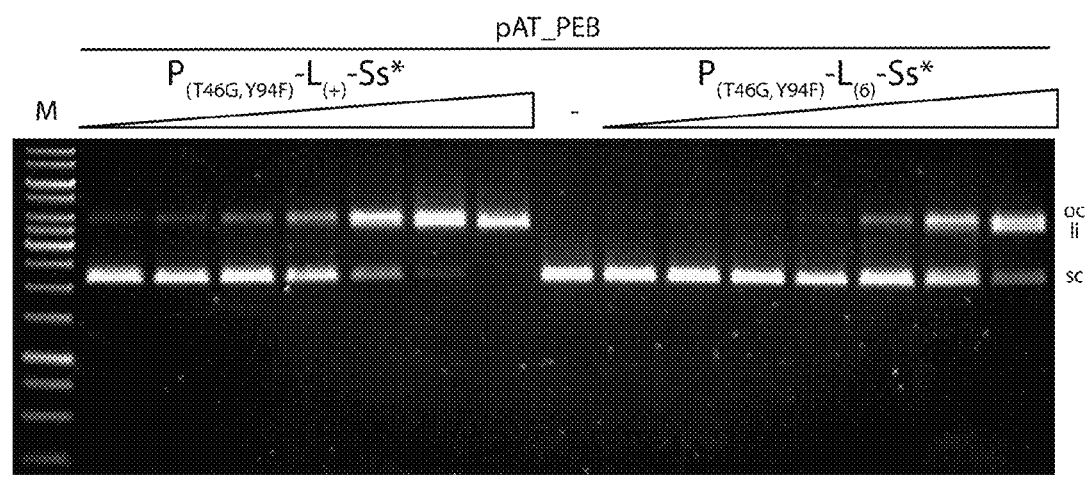

8 nM linearized plasmid DNA containing the addressed site with an additional unaddressed PvuII site (S6P6S_P; A) or supercoiled plasmid DNA containing just a PvuII site (B) were incubated with fusion enzyme ranging from 4-256 nM in optimized KG Buffer overnight (~16 h). The reactions were analyzed on 0.8% agarose gels. Results are shown in FIG. 2.

Figure 3:
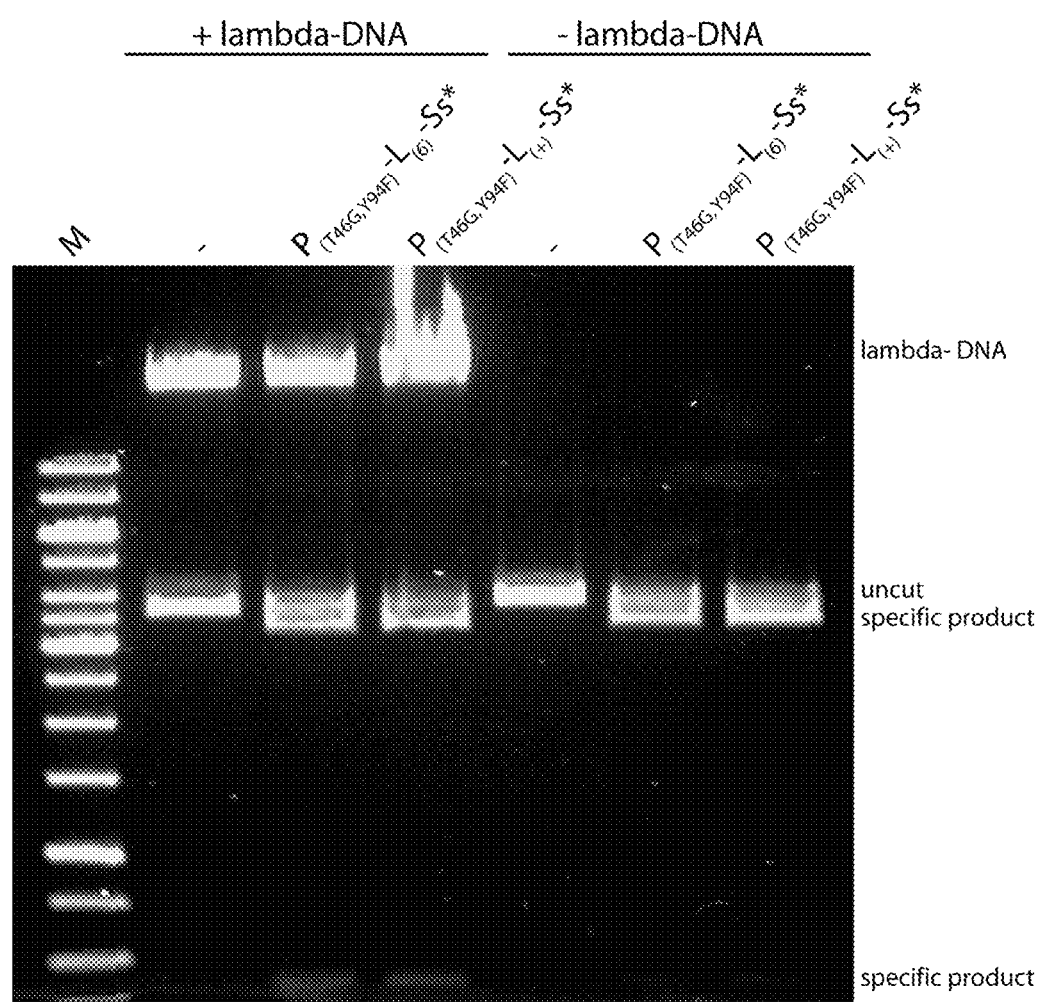
FIG. 3 shows an agarose gel analysis for determining cleavage products of the L(6) (SEQ ID NO: 9) and L(+) (SEQ ID NO: 10) variants of the polypeptide of the present invention in the presence or absence of bacteriophage lambda competitor DNA. Cleavage occurs independently of the presence of bacteriophage lambda DNA.

8 nM linearized plasmid DNA (S6P6S_P) were incubated with 8 nM fusion enzyme in optimized KG Buffer for 3 h at 37° C. either in the presence or absence of 940 pM λ-DNA which contains 15 PvuII sites. The reaction was analyzed on 0.8% agarose gel. Results are shown in FIG. 3.

Figure 4:
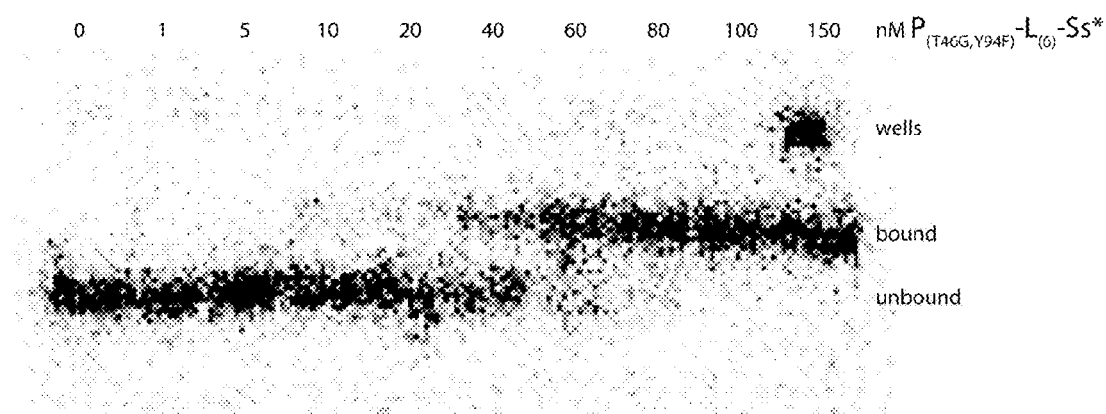
FIG. 4 shows an electrophoretic mobility shift analysis (EMSA). (A) the tripartite DNA recognition site I-SceI-PvuII-I-SceI is bound by the fusion protein L(6); (b) and (C) no binding occurs at only the I-SceI DNA recognition site (B) or the PvuII DNA recognition site (C).
Figure 4:
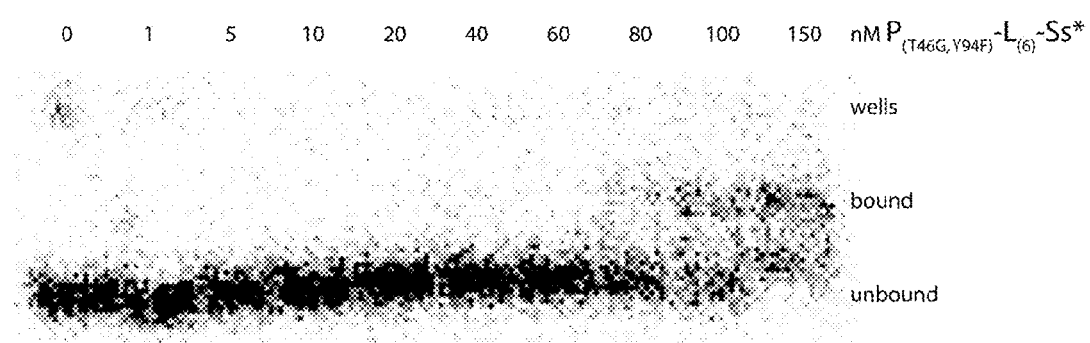
Figure 4:
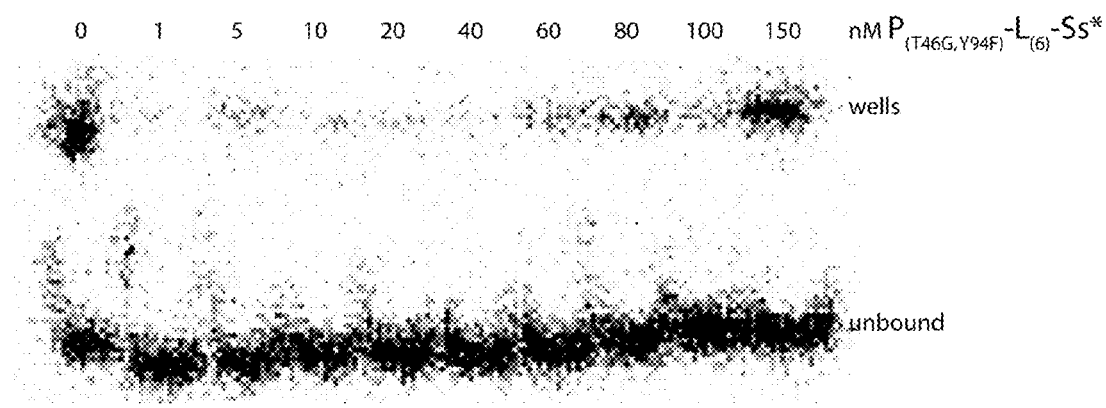

For the determination of binding constants of the fusion enzymes, EMSAs with radioactive labeled PCR-fragments were done. The shift fragments were created via PCR using [α$^{32}$P] dATP. One fragment contained the addressed site (S6P6S; A), just an I-SceI site (S; B) or just a PvuII site (P; C). 2 nM of the radiolabeled substrate were incubated with fusion enzyme at concentrations ranging from 1-150 nM in optimized KG Buffer without magnesium for 30 min at room temperature. After adding 1 µl 87% glycerol the samples were loaded onto a 6% polyacrylamid Tris-Acetate (pH 8.5) gel and run for 2 h at 10V/cm. The bands were visualized using the InstantImager system (Packard). Results are shown in FIG. 4.

Electrocompetent *E. coli* cells either harboring the plasmid coding for M.PvuII or not were transformed with 50 ng plasmid coding for PvuII_wt or one of the fusion enzymes. 50 µl of the transformation mixture were spread on agar-plates containing the corresponding antibiotics and incubated overnight at 37° C. Results are shown in FIG. 5.

8 nM linearized plasmid DNA (S6P6S_P) were incubated with 8 nM of the fusion enzymes with the ΔC9 I-SceI (SEQ ID 9 &10) or the fusion enzymes with full length I-SceI in optimized KG Buffer for 1 h at 37° C. The reactions were analyzed on 0.8% agarose gels. Results are shown in FIG. 6.

The invention claimed is:

1. A polynucleotide encoding a polypeptide comprising:
   (i) a first module comprising at least a first DNA binding domain from I-SceI, wherein the first module comprises (a) the amino acid sequence of SEQ ID NO:1 or (b) the amino acid sequence of SEQ ID NO:1 having one or more of the following changes: (1) substitution D44S, (2) substitution D44S in combination with D145A, (3) substitution D44N in combination with D145A, (4) a deletion of 5 to 9 amino acids from the C-terminal end;
   (ii) a linker; and
   (iii) a second module comprising at least a second DNA binding domain and a cleavage domain from PvuII, wherein the second module comprises (a) the amino acid sequence of SEQ ID NO:2 or (b) the amino acid sequence of SEQ ID NO:2 having one of the following changes: (1) substitution T46G, (2) substitution H83A, (3) substitution Y94F, (4) substitution T46G in combination with H83A, (5) substitution T46G in combination with Y94F, or (6) substitution T46G in combination with H83A and Y94F;
   wherein said polypeptide functionally interacts only with DNA comprising a DNA recognition site for the first DNA binding domain and a DNA recognition site for the second DNA binding domain, and
   wherein said cleavage domain cleaves DNA within a specific DNA cleavage site upon binding of the polypeptide.

2. The polynucleotide of claim 1, wherein said specific DNA cleavage site and said DNA recognition site of the second DNA binding domain of the restriction endonuclease are identical.

3. The polynucleotide of claim 1, wherein said second DNA binding domain and the cleavage domain comprised in the second module are derived from a type IIP restriction endonuclease.

4. The polynucleotide of claim 1, wherein said second DNA binding domain and the cleavage domain comprised in the second module are derived from a restriction endonuclease which exhibits reduced DNA binding and/or reduced catalytic activity when compared to the wild type restriction endonuclease.

5. The polynucleotide of claim 1, wherein said first module exhibits reduced or no catalytic activity.

6. The polynucleotide of claim 1, wherein said linker consists essentially of 6 to 10 amino acids.

7. The polynucleotide of claim 6, wherein said linker has an amino acid sequence of SEQ ID NO: 3 or SEQ ID NO: 4.

8. A vector comprising the polynucleotide of claim 1.

9. A microorganism, a plant, plant part or isolated cell thereof; or an isolated animal tissue or isolated cell thereof comprising the polynucleotide of claim 1.

10. The polynucleotide of claim 1, wherein the polynucleotide encodes a polypeptide having the amino acid sequence of SEQ ID NO: 9.

11. The polynucleotide of claim 1, wherein the polynucleotide encodes a polypeptide having the amino acid sequence of SEQ ID NO: 10.

* * * * *